US006534062B2

(12) United States Patent
Raz et al.

(10) Patent No.: US 6,534,062 B2
(45) Date of Patent: Mar. 18, 2003

(54) METHODS FOR INCREASING A CYTOTOXIC T LYMPHOCYTE RESPONSE IN VIVO

(75) Inventors: Eyal Raz, Del Mar, CA (US); Hearn Jay Cho, New York, NY (US); Douglas Richman, La Jolla, CA (US); Anthony A. Horner, San Diego, CA (US)

(73) Assignees: The Regents of the University of California, Oakland, CA (US); The United States of America as represented by the Department of Veterans Affairs, Washington, DC (US)

( * ) Notice: Subject to any disclaimer, the term of this patent is extended or adjusted under 35 U.S.C. 154(b) by 0 days.

(21) Appl. No.: 09/820,484

(22) Filed: Mar. 28, 2001

(65) Prior Publication Data
US 2002/0142977 A1 Oct. 3, 2002

Related U.S. Application Data
(60) Provisional application No. 60/192,537, filed on Mar. 28, 2000, provisional application No. 60/203,567, filed on May 11, 2000, and provisional application No. 60/215,895, filed on Jul. 5, 2000.

(51) Int. Cl.⁷ ........................ A61K 39/385; C07H 21/04
(52) U.S. Cl. .................... 424/193.1; 536/23.1; 536/24.1
(58) Field of Search ............................. 536/23.1, 24.1; 424/193.1

(56) References Cited

U.S. PATENT DOCUMENTS 6,406,705 B1 * 6/2002 Davis et al. .............. 424/278.1

FOREIGN PATENT DOCUMENTS

WO    WO 98/16247    4/1998
WO    WO 00/20039    4/2000

OTHER PUBLICATIONS

Alkhatib et al. (1996) "CC CKR5: A RANTES, MIP–1 α, MIP–1β receptor as a Fusion Cofactor for Macrophage–Tropic HIV–1." *Science*, vol. 272:1955–1958.
Bauer et al. (1999) "DNA activates human immune cells through a CpG sequence–dependent manner." *Immunology*, vol. 97:699–705.
Bennett et al. (1998) "Help for cytotoxic–T–cell responses is mediated by CD40 signalling." *Nature*, vol. 393:478–480.
Carson et al. (1997) "Oligonucleotide Adjuvants for T Helper 1 (Th1)–specific Vaccination." *J. Exp. Med.*, vol. 186 (10): 1621–1622.
Cho et al. (2000) "Immunostimulatory DNA–based vaccines induce cytotoxic lymphocyte activity by a T–helper cell–independent mechanism." *Nature Biotechnology*, vol. 18:509–514.

Choe et al. (1996) "The β–Chemokine receptors CCR3 and CCR5 Facilitate Infection by Primary HIV–1 Isolates." *Cell*, vol. 85:1135–1148.
Chu et al. (2000) "DNA–PKcs is Required for Activation of Innate Immunity by Immunostimulatory DNA." *Cell*, vol. 103:909–918.
Cocchi et al. (1995) "Identification of RANTES, MIP–1α, and MIP–1β as the Major HIV–Suppressive Factors Produced by CD8+ T cells." *Science*, vol. 270:1811–1815.
Corr et al. (1996) "Gene Vaccination with Naked Plasmid DNA: Mechanism of CTL Priming." *J. Exp. Med.*, vol. 184:1555–1560.
Deng et al. (1996) "Identification of a major co–receptor for primary isolates of HIV–1." *Nature*, vol. 381:661–666.
Dragic et al. (1996) "HIV–1 entry into CD4+ cells is mediated by the chemokine receptor CC–CKR–5." *Nature*, vol. 381:667–673.
Grewal et al. (1996) "The Role of CD40 Ligand in Costimulation and T–cell Activation." *Immunological Reviews*, No. 153:85–106.
Harding et al. (1993) "CD28–B7 Interactions Allow the Induction of CD8+ Cytotoxic T Lymphocytes in the Absence of Exogenous Help." *J. Exp. Med.*, vol. 177:1791–1796.
Hemmi et al. (2000) "A Toll–like receptor recognizes bacterial DNA." *Nature*, vol. 408:740–745.
Horner et al. (1998) "Immunostimulatory DNA is a Potent Mucosal Adjuvant." *Cellular Immunology*, vol. 190:77–82.
Keene et al. (1982) "Helper Activity is Required for the in vivo generation of Cytotoxic T Lymphocytes." *J. Exp. Med.*, vol. 155:768–782.
Moss et al. (2000) "In vitro immune function after vaccination with an inactivated, gp120–depleted HIV–1 antigen with immunostimulatory oligodeoxynucleotides." *Vaccine*, vol. 18:1081–1087.
Ridge et al. (1998) "A conditioned dendritic cell can be a temporal bridge between a CD4+ T–helper and a T–killer cell." *Nature*, vol. 393:474–478.

(List continued on next page.)

Primary Examiner—James Ketter
Assistant Examiner—Celine Qian
(74) Attorney, Agent, or Firm—Paula A. Borden; Bozicevic, Field & Francis, LLP

(57) ABSTRACT

The invention provides methods for T helper-independent activation of an antigen-specific cytotoxic T lymphocyte response in an individual. The methods generally involve administering to an individual an immunostimulatory nucleic acid molecule in an amount effective to increase an antigen-specific CTL response in the individual. The invention further provides methods for increasing chemokine secretion, which can block HIV infection.

11 Claims, 20 Drawing Sheets

OTHER PUBLICATIONS

Schoenberger et al. (1998) "T–cell help for cytotoxic T lymphocytes is mediated by CD40–CD40L interactions." *Nature*, vol. 393:480–483.

Sigal et al. (1998) "The Role of B7–1 and B7–2 Costimulation for the Generation of CTL Responses in vivo." *The Journal of Immunology*, vol. 161:2740–2745.

Sparwasser et al. (1998) "Bacterial DNA and immunostimulatory CpG oligonucleotides trigger maturation and activation of murine dendritic cells." *Eur. J. Immunol.*, vol. 28:2045–2054.

Tokunaga et al. (1984) "Antitumor Activity of Deoxyribonucleic Acid Fraction From *Mycobactrium bovis* BCG. I. Isolation, Physicochemical Characterization, and Antitumor Activity." *JNGI*, vol. 72(4):955–962.

Yamamoto et al. (1992) "DNA from Bacteria, but Not from Vertebrates, induces Interferons, Activates Natural Killer Cells and Inhibits Tumor Growth." *Microbiol. Immunol.*, vol. 36(9):983–997.

* cited by examiner

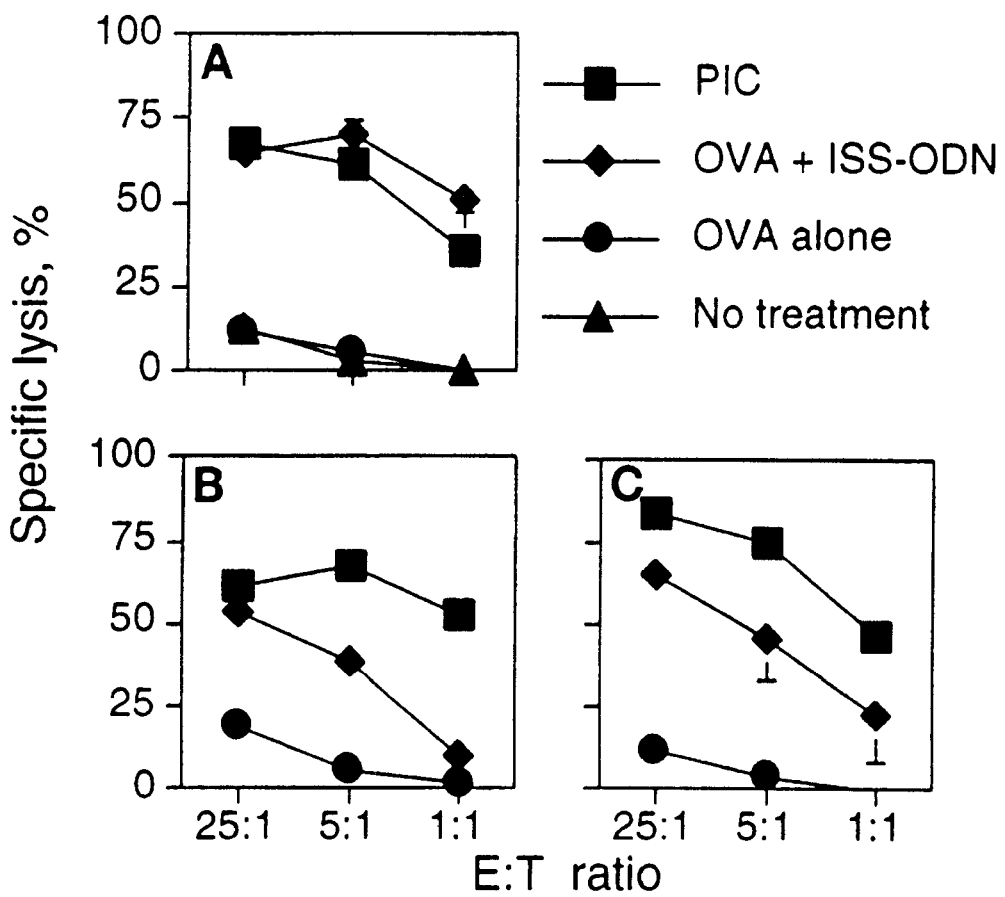

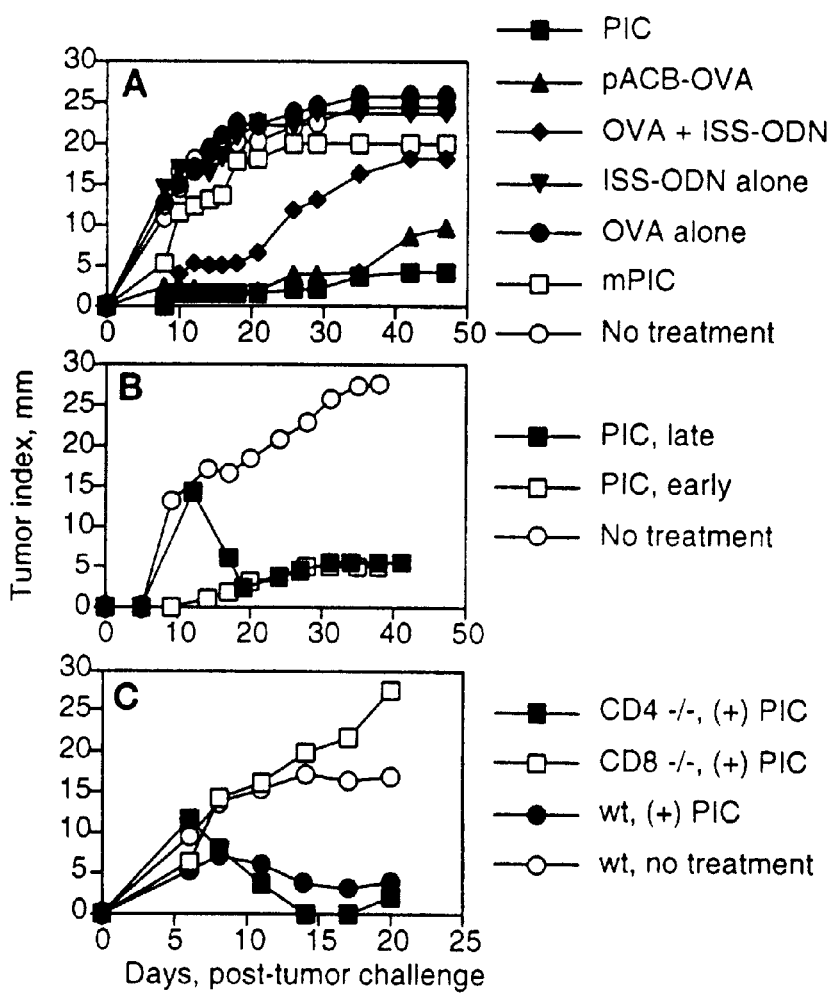

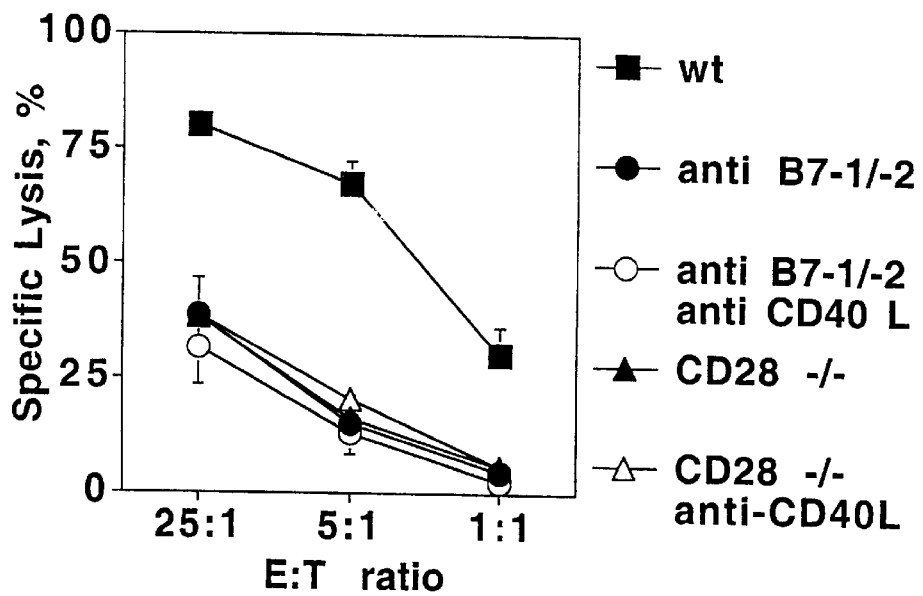
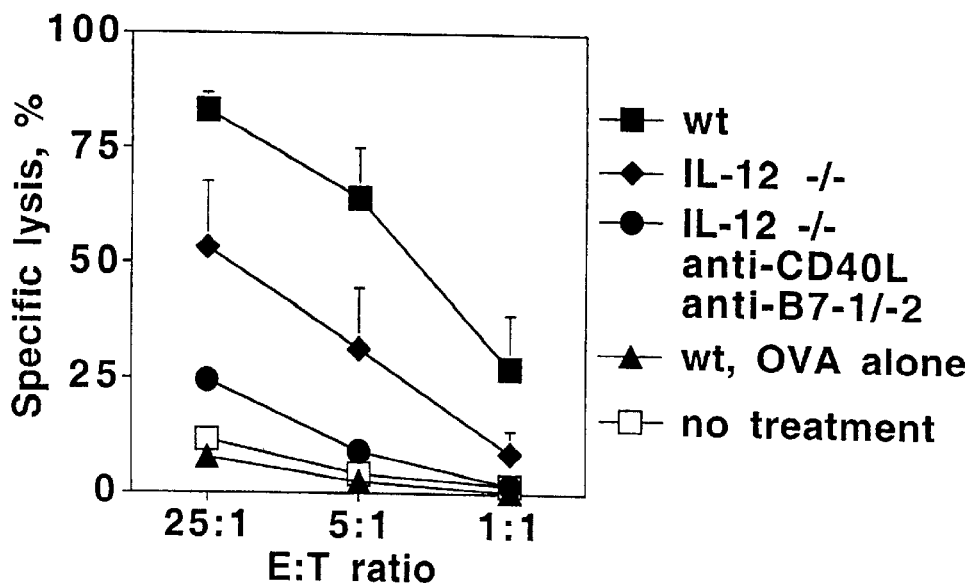

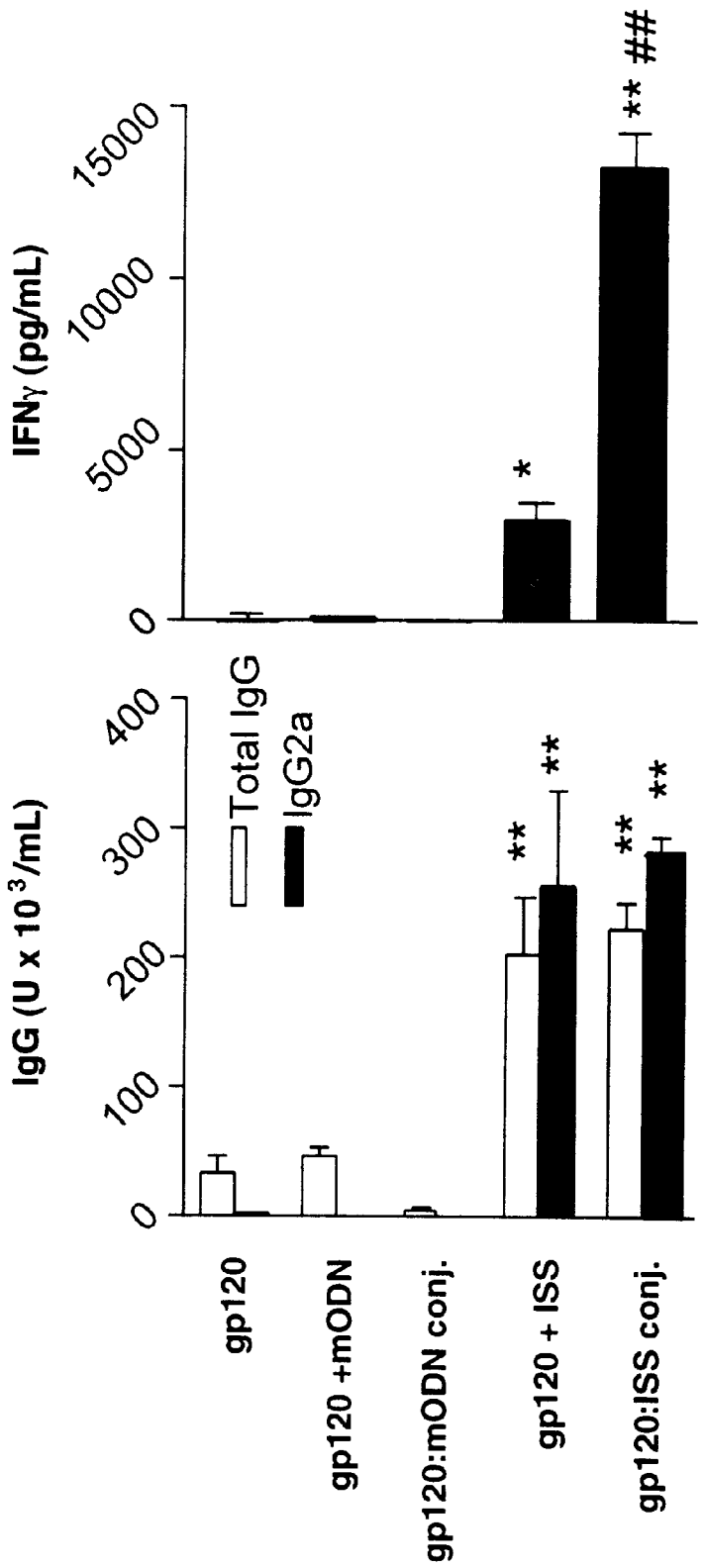

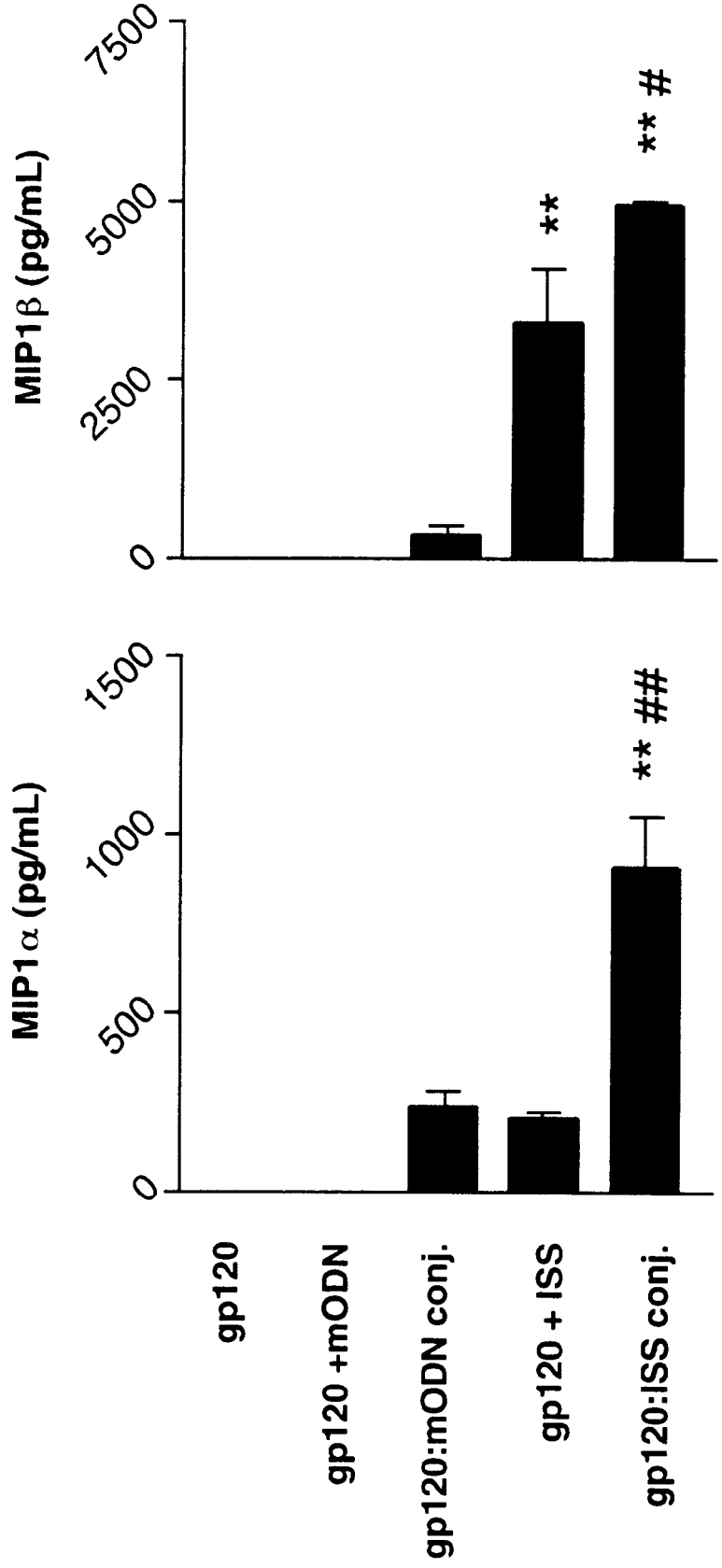

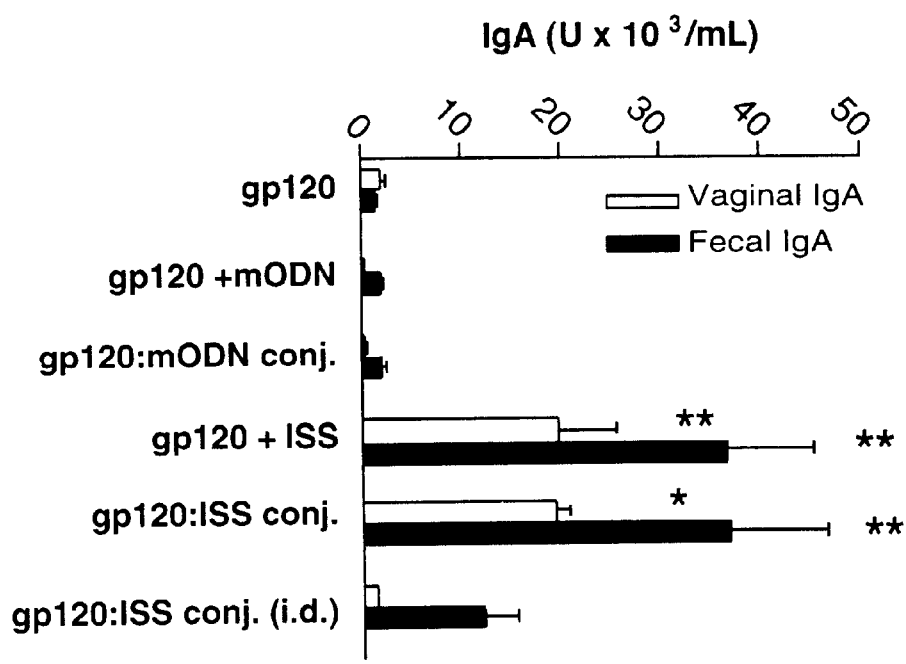

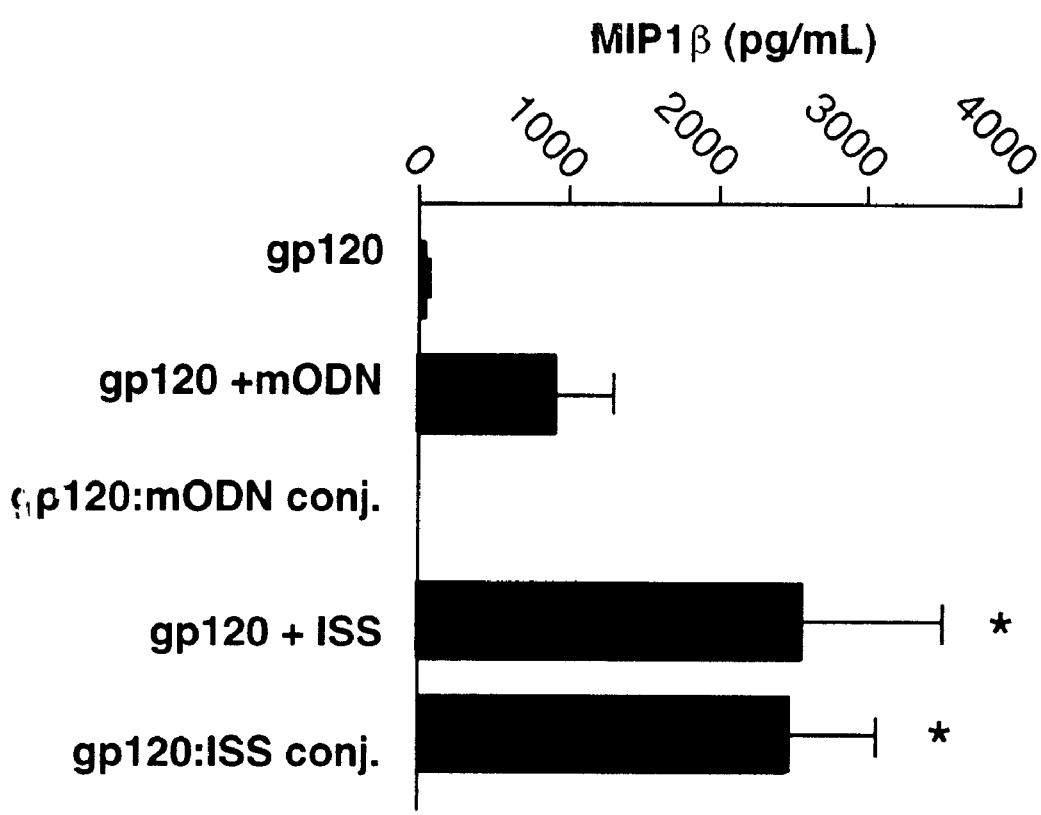

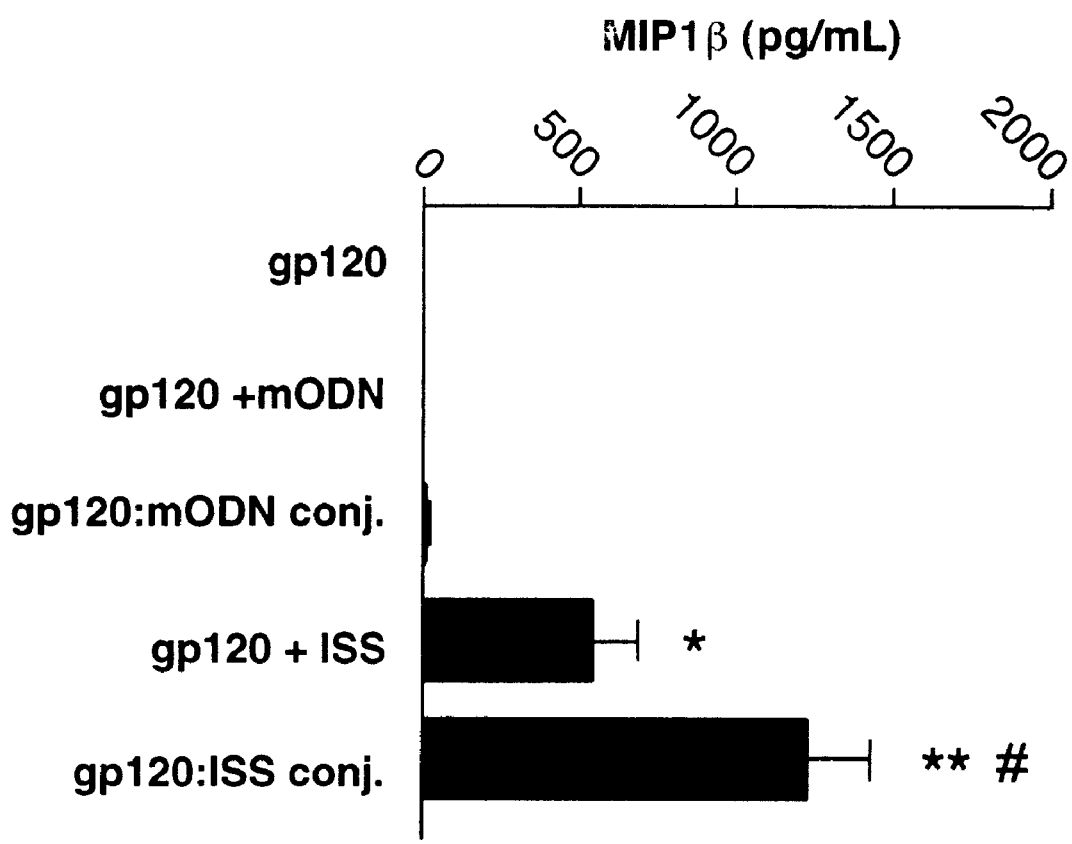

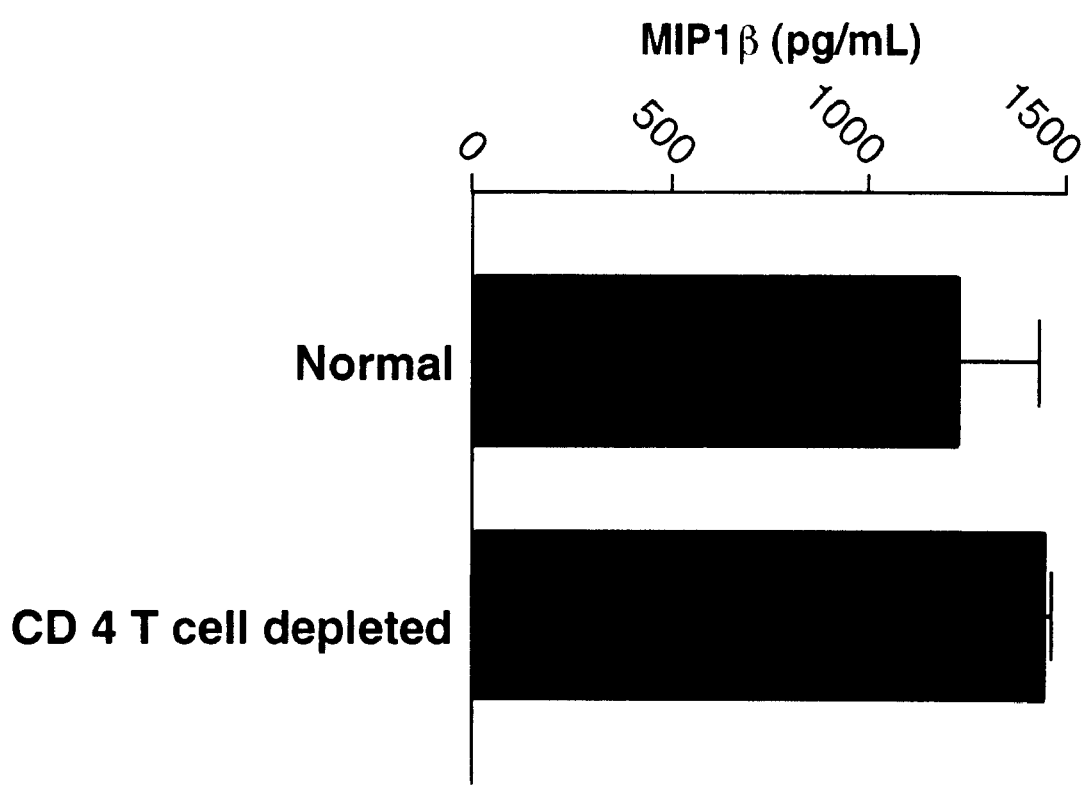

SEQUENCE LISTING

```
<160> NUMBER OF SEQ ID NOS: 8

<210> SEQ ID NO 1
<211> LENGTH: 22
<212> TYPE: DNA
<213> ORGANISM: Artificial Sequence
<220> FEATURE:
<223> OTHER INFORMATION: Disulfide-linked phosphorothioate ISS-ODN
<221> NAME/KEY: modified_base
<222> LOCATION: (1)...(1)
<223> OTHER INFORMATION: disulfide thymine

<400> SEQUENCE: 1
tgactgtgaa cgttcgagat ga                                        22

<210> SEQ ID NO 2
<211> LENGTH: 22
<212> TYPE: DNA
<213> ORGANISM: Artificial Sequence
<220> FEATURE:
<223> OTHER INFORMATION: mutated ODN
<221> NAME/KEY: modified_base
<222> LOCATION: (1)...(1)
<223> OTHER INFORMATION: disulfide thymine

<400> SEQUENCE: 2
tgactgtgaa ccttcgagat ga                                        22

<210> SEQ ID NO 3
<211> LENGTH: 22
<212> TYPE: DNA
<213> ORGANISM: Artificial Sequence
<220> FEATURE:
<223> OTHER INFORMATION: phosphorothioate ISS-ODN

<400> SEQUENCE: 3
tgactgtgaa cgttcgagat ga                                        22

<210> SEQ ID NO 4
<211> LENGTH: 8
<212> TYPE: PRT
<213> ORGANISM: Artificial Sequence
<220> FEATURE:
<223> OTHER INFORMATION: OVA peptide

<400> SEQUENCE: 4

Ser Ile Ile Asn Phe Glu Lys Leu
 1               5

<210> SEQ ID NO 5
<211> LENGTH: 9
<212> TYPE: PRT
<213> ORGANISM: Artificial Sequence
<220> FEATURE:
<223> OTHER INFORMATION: Influenza virus nucleoprotein peptide

<400> SEQUENCE: 5

Ala Ser Asn Glu Asn Met Glu Thr Met
 1               5

<210> SEQ ID NO 6
<211> LENGTH: 22
<212> TYPE: DNA
<213> ORGANISM: Artificial Sequence
<220> FEATURE:
<223> OTHER INFORMATION: mutated control ODN
```

```
<400> SEQUENCE: 6
tgactgtgaa ccttcgagat ga                                              22

<210> SEQ ID NO 7
<211> LENGTH: 22
<212> TYPE: DNA
<213> ORGANISM: Artificial Sequence
<220> FEATURE:
<223> OTHER INFORMATION: mODN

<400> SEQUENCE: 7
tgactgtgaa ccttagagat ga                                              22

<210> SEQ ID NO 8
<211> LENGTH: 10
<212> TYPE: PRT
<213> ORGANISM: Artificial Sequence
<220> FEATURE:
<223> OTHER INFORMATION: HIV-1 class I-restricted gp120 peptide

<400> SEQUENCE: 8

Arg Gly Pro Gly Arg Ala Phe Val Thr Ile
 1               5                  10
```

METHODS FOR INCREASING A CYTOTOXIC T LYMPHOCYTE RESPONSE IN VIVO

CROSS-REFERENCE TO RELATED APPLICATIONS

This application claims the benefit of U.S. Provisional Patent Application Ser. No. 60/192,537, filed Mar. 28, 2000; U.S. Provisional Patent Application Ser. No. 60/203,567, filed May 11, 2000; and U.S. Provisional Patent Application Ser. No. 60/215,895, filed Jul. 5, 2000, which applications are each incorporated herein by reference in their entirety.

GOVERNMENT RIGHTS

The United States Government may have certain rights in this application pursuant to National Institutes of Health Grant Nos. AI40682 and A147078.

FIELD OF THE INVENTION

This invention relates to methods of modulating an immune response, and in particular to methods of increasing an antigen-specific cytotoxic T lymphocyte response.

BACKGROUND OF THE INVENTION

Immunostimulatory nucleic acid molecules were initially discovered in the mycobacterial genome as DNA sequences that selectively enhance NK cell activity (Yamamoto, et al. (1992) *Microbiol. Immunol.* 36:983–997). Uptake of mycobacterial DNA or has been shown to activate cells of the innate immune system, such as NK cells and macrophages and stimulating a type-1 like response (Roman, et al. (1997) *Nature Med.* 3:849–854). Further, administration of immunostimulatory nucleic acid molecules has been shown to induce B cell proliferation (Messina, et al. (1991) *J. Immunol.* 147:1759–1764), stimulate production of cytokines, such as interferons (IFNs), IL-12, IL-18 and TNF-α (Sparwasser, et al. (1998) *Eur. J. Immunol.* 28:2045–2054; Sparwasser, et al. (1997) *Eur. J. Immunol.* 27:1671–1679; Stacey, et al. (1996) *J. Immunol.* 157:2116–2122) and up-regulate co-stimulatory receptors (Martin-Orozco, et al. (1999) *Int. Immun.* 11:111–118; Sparwasser, et al. (1998) *Eur. J. Immunol.* 28:2045–2054) by these cells.

Cytotoxic T Lymphocytes (CTL) are critical effector cells in the control of cells infected with intracellular pathogens and in the control of MHC class I+ tumors. Induction of CTL is a primary goal of many vaccine strategies. Accumulating evidence indicates that one of the pathways of CTL priming in vivo is through "cross-priming," which involves the uptake and re-presentation of soluble, exogenous antigens by bone marrow-derived antigen-presenting cells (APCs), e.g., dendritic cells. Depending on the activation state of the "cross-presenting" APC, responding T cells can either be activated or tolerized. The nature of the specific requirements for these disparate outcomes is currently a topic of intense interest, as elucidation of such would aid in the design of vaccines as well as in the modulation of anti-tumor CTL responses. Current models of cross-priming consist of two steps; a "licensing" interaction between antigen presenting cells (APC) and helper T cells ($T_h$), followed by an activating interaction between "licensed" APC and cytotoxic T lymphocytes (CTL). Thus, in current models, there is a requirement for $T_h$ cells in cross-priming of CTL.

Immunodeficiency can arise from a variety of causes, including primary immunodeficiencies, e.g., due to a heritable defect; and acquired immunodeficiencies, e.g., due to cancer chemotherapy, or due to infection with a pathogen, e.g., human immunodeficiency virus. Immunodeficient individuals are more vulnerable to infectious diseases than individuals with healthy immune systems. Antibiotics can control bacterial infections, but long-term treatment with antibiotics is not without risk of adverse side effects. Control of intracellular pathogens, including viruses, bacteria, and protozoans, poses a greater challenge for treatment. Immunodeficient individuals may also be more vulnerable to growth of cancer cells than individuals with healthy immune systems. Treatment of these individuals with conventional anti-cancer therapeutic agents is not always feasible.

The current methodologies for inducing a CTL response include vaccines which use attenuated viruses or DNA vaccines. There is a need in the art for more effective ways of increasing an antigen-specific CTL response in an individual. Furthermore, there is a need in the art for alternative methods of enhancing immune functions in immunodeficient individuals. The present invention addresses these needs by providing methods for increasing cytotoxic T lymphocyte (CTL) activity. The methods are useful for increasing an antigen-specific CTL response in an individual to any soluble antigen. The methods are also useful for increasing an antigen-specific CTL response in $CD4^+$-deficient individuals and individuals at risk for becoming $CD4^+$ deficient.

SUMMARY OF THE INVENTION

The invention provides methods for T helper-independent activation of an antigen-specific cytotoxic T lymphocyte response in an individual. The methods generally involve administering to an individual an immunostimulatory nucleic acid molecule in an amount effective to increase an antigen-specific CTL response in the individual. The invention further provides methods for increasing chemokine secretion, which can block HIV infection.

The methods are useful for generating both a CTL response and a humoral response to a soluble exogenous antigen. Thus, an immunostimulatory nucleic acid molecule, when administered together with a soluble, exogenous antigen, results in cross-priming of CTLs. Therefore, the methods are useful in generating an immune response, particularly a CTL response, to a cell infected with an intracellular pathogen, or to a tumor cell expressing a tumor-specific or tumor-associated antigen.

The methods are also useful in treating individuals with a reduced number of functional $CD4^+$ T cells ("$CD4^+$-deficient individuals" or "$CD4^+$-low individuals") compared to normal individuals, e.g. individuals affected by an acquired or primary immunodeficiency, as well as those at risk for becoming immunodeficient.

The immunostimulatory nucleic acid molecules may be administered in a formulation alone, or together with an antigen, e.g., admixed or linked or conjugated to an antigen or antigenic epitope. In many embodiments, the antigen is a soluble, exogenous antigen. The methods are useful in stimulating, or increasing antigen-specific CTL activity to any of a variety of target antigens, e.g., an antigen expressed in a cell, or an antigen expressed on the surface of a cell or cell population. In some embodiments, methods are provided for increasing CTL activity toward pathogen-infected cells. In other embodiments, methods are provided for increasing CTL activity toward a tumor cell.

The invention further provides methods for increasing tumor-specific immunity in an individual. The methods generally involve administering to an individual an immunostimulatory nucleic acid molecule in an amount effective to increase tumor-specific immunity in an individual. The methods are useful to treat cancer, e.g., to inhibit the growth of cancer cells. The methods are also useful as a preventive measure, e.g., to inhibit the probability that cancerous cell growth will occur, or that a previously treated cancer will recur. The methods are particularly useful for decreasing a tumor load in a CD4+ T-cell deficient individual, and in individuals at risk for becoming CD4+ deficient.

The invention further provides methods of immunizing against and/or treating an infectious disease in an individual. The methods generally involve administering to an individual an immunostimulatory nucleic acid molecule in an amount effective to increase antigen-specific CTL activity. The methods are particularly useful in immunizing against and/or treating infectious diseases due to intracellular pathogens. The methods are also useful for treating infectious disease in a CD4+ T-cell deficient individual, and in individuals at risk for becoming CD4+ deficient.

The present invention further provides compositions and methods for increasing secretion of a chemokine from a eukaryotic cell, which in turn inhibits infection of a cell by pathogens that establish infection in a host, or cause disease by, interaction with a chemokine receptor. The methods generally involve contacting a cell with a composition comprising an immunostimulatory nucleic acid molecule. Accordingly, the invention further provides methods of reducing infection of a cell by a pathogen, comprising contacting a cell with an immunostimulatory nucleic acid molecule such that chemokine secretion is increased, and infection is reduced. Chemokine secretion may be antigen specific, where both immunostimulatory nucleic acid molecule and antigen are administered, or antigen non-specific, where immunostimulatory nucleic acid molecule is administered in the absence of exogenously provided antigen.

Immunostimulatory nucleic acid molecules induce secretion of chemokines that bind to chemokine receptors. Certain chemokine receptors are used by pathogenic microorganisms to enter and infect a cell. Increasing synthesis of such chemokines serves to competitively inhibit binding of the pathogenic microorganism to the chemokine receptor. Accordingly, in further aspects, the present invention provides compositions and methods for increasing secretion of a chemokine from a eukaryotic cell, which in turn inhibits infection of a cell by pathogens that establish infection in a host, or cause disease by, interaction with a chemokine receptor. The methods generally involve contacting a cell with a composition comprising an immunostimulatory nucleic acid molecule. Accordingly, the invention further provides methods of reducing infection of a cell by a pathogen, comprising contacting a cell with an immunostimulatory nucleic acid molecule such that chemokine secretion is increased, and infection is reduced. Chemokine secretion may be antigen specific, where both immunostimulatory nucleic acid molecule and antigen are administered, or antigen non-specific, where immunostimulatory nucleic acid molecule is administered in the absence of exogenously provided antigen.

These and other objects, advantages, and features of the invention will become apparent to those persons skilled in the art upon reading the details of the invention as more fully described below.

BRIEF DESCRIPTION OF THE DRAWINGS

FIGS. 3A–C are graphs depicting MHC Class-I restricted CTL activation in CD4 –/– by protein-ISS conjugates in wild type (FIG. 3A), CD4–/– (FIG. 3B), and MHC class II–/– (FIG. 3C) mice. Mice were injected intradermally on days zero and 14 with either protein-ISS conjugate (squares); OVA+ISS (diamonds); or OVA alone (circles).

FIGS. 4A–C are graphs depicting protective immunity conferred by vaccination with protein-ISS conjugates in preventive and therapeutic models of cancer.

FIG. 7 is a graph depicting specific lysis versus effector:target ratio for CTL from wild-type injected with ISS+OVA (wt); wild-type mice pre-treated with anti-B7-1/-2 and injected with ISS+OVA (anti B7-1/-2); wild-type mice pre-treated with anti-B7-1/-2 and anti-CD40 ligand antibody, and injected with ISS+OVA (anti B7-1/-2; anti CD40 L); CD28$^{-/-}$ mice injected with ISS+OVA; and CD28$^{-/-}$ mice pre-treated with anti-CD40 ligand antibody, and injected with ISS+OVA (CD28$^{-/-}$; anti-CD40L).

FIG. 8 is a graph depicting specific lysis versus effector:target ratio for CTL from wild-type injected with ISS+OVA (wt); IL-12$^{-/-}$ mice injected with ISS+OVA; IL-12$^{-/-}$ mice pre-treated with anti-CD40L antibody and anti-B7-1/-2 antibody, then injected with ISS+OVA (IL-12$^{-/-}$; anti-CD40L; anti-B7-1/-2); wild-type mice injected with OVA alone (wt, OVA alone); and wild-type mice not injected with ISS+OVA (no treatment).

FIGS. 12A–D are graphs depicting antigen-specific immunoglobulin (FIG. 12A), cytokine (FIG. 12B), and chemokine (FIGS. 12C and 12D) responses in mice injected intradermally with ISS-based gp120 vaccines.

DETAILED DESCRIPTION OF THE INVENTION

Figure 1:
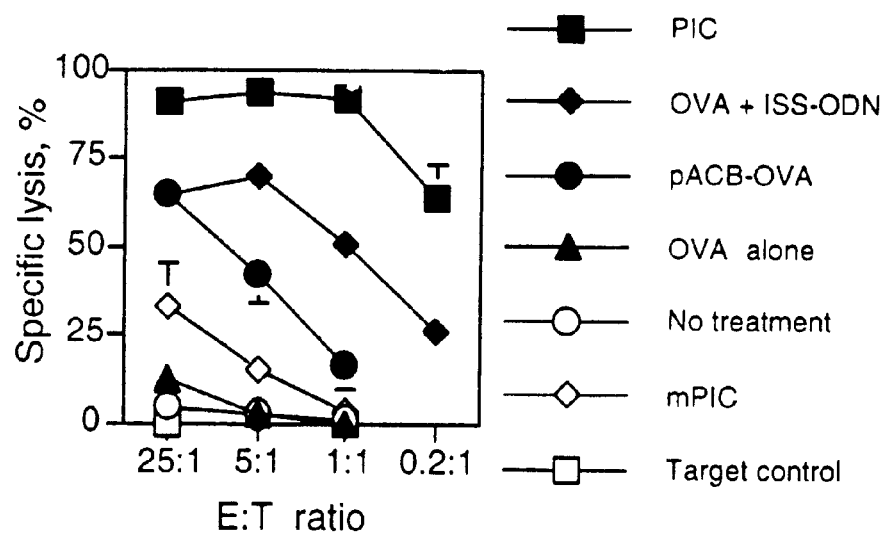
FIG. 1 is a graph depicting the effect of vaccination with protein-ISS conjugates on antigen-specific CTL activity. Animals were injected intradermally with protein-ISS conjugate (open squares), using hen egg ovalbumin (OVA) as a model antigen; OVA+ISS (open diamonds); pACB-OVA (closed circles); OVA alone (closed triangles); protein-mutated ISS conjugate (open diamonds); or target control (open squares). Open circles indicate no treatment.

The immune system can react to the presence of a foreign antigen by generating antigen-specific CD4$^+$ (helper) T cells and CD8$^+$ (cytotoxic) T cells. CD4$^+$ T cells are sometimes classified as Th1 or Th2, depending on the cytokine profile produced. The present invention relates to the observation that an immunostimulatory nucleic acid molecule can stimulate an antigen-specific cytotoxic T lymphocyte (CTL) response even in the absence of CD4$^+$ T helper cells. This observation is counter to the accepted model of a requirement for CTL activation. Current models posit that an antigen-presenting cell (APC), must have an initial "licensing" interaction with Th cells before the Th cells can activate CTL. Previous work describing the APC response to immunostimulatory nucleic acid molecule stimulation (e.g., upregulation of cytokines and co-stimulatory molecules) suggested that APCs deliver the stimulatory signal to T helper cells. The present inventors have made the surprising discovery that, contrary to this model, immunostimulatory nucleic acid molecules are capable of increasing an antigen-specific CTL response, even in the absence of in a CD4$^+$ T lymphocytes. In addition, immunostimulatory nucleic acid molecules increase chemokine secretion, which chemokines are competitive inhibitors of HIV for binding to HIV receptors.

Without wishing to be bound by theory, immunostimulatory nucleic acid molecules may replace some or all of the "licensing" effects on APCs, indicating that the Th1 phenotype and CTL activation are independent, rather than linked. Thus, the immunostimulatory nucleic acid molecule allows the APC to activate directly antigen-specific CTL activity. The present inventors' observations thus make it possible, for the first time, to use immunostimulatory nucleic acid molecules to increase a CTL response in CD4$^+$ T helper cell-deficient individuals.

Accordingly, the present invention provides methods of inducing or increasing antigen-specific CTL activity in an individual via cross-presentation, comprising administering an immunostimulatory nucleic acid molecule and a soluble exogenous antigen to the individual. The methods generally involve administering to an individual an immunostimulatory nucleic acid molecule, which may optionally be administered with an antigen, particularly a soluble exogenous antigen. The methods can be used to increase or induce a CTL response to various undesired cells or cell populations, e.g., pathogen-infected cells, and tumor cells.

The invention further provides methods of inducing CTL activity in CD4-deficieint individuals or to individuals with a healthy, intact immune system, but who are at risk for becoming CD4$^+$ deficient. The methods generally involve administering to an individual an immunostimulatory nucleic acid molecule (which may optionally be administered with an antigen, particularly a soluble exogenous antigen), and are useful in increasing or inducing a CTL response to various undesired cells or cell populations, e.g., pathogen-infected cells, and tumor cells.

The present invention further provides compositions and methods for increasing chemokine secretion from a eukaryotic cell, particularly to inhibit infection of the cell by a pathogen that establishes infection or otherwise causes disease or symptoms of disease in a host by interaction with a chemokine receptor. This aspect of the invention is based on the unexpected discovery that certain polynucleotides, termed immunostimulatory nucleic acid molecules, can increase secretion of chemokines from cells that normally produce chemokines. For example, increased chemokine production, particularly of chemokines that bind HIV co-receptors, can reduce the incidence of HIV entry into a cell. Thus, the invention further provides methods of reducing susceptibility to infection of a susceptible eukaryotic cell by a pathogen, as well as methods for treating an infection by a pathogen. The methods involve administering an immunostimulatory nucleic acid molecule to an individual to increase secretion of a chemokine that binds to a chemokine receptor which serves as a co-receptor for infection by a pathogen. The secreted chemokine binds to the chemokine receptor and reduces pathogen entry into the cell, or otherwise reduces the undesirable effects of pathogen interaction with the cell.

Before the present invention is described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "and", and "the" include plural referents unless the context clearly dictates otherwise. Thus, for example, reference to "an immunostimulatory nucleic acid molecule" includes a plurality of such molecules and reference to "the tumor cell" includes reference to one or more tumor cells and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Definitions

The terms "oligonucleotide," "polynucleotide," and "nucleic acid molecule", used interchangeably herein, refer to a polymeric forms of nucleotides of any length, either ribonucleotides or deoxyribonucleotides. Thus, this term includes, but is not limited to, single-, double-, or multi-stranded DNA or RNA, genomic DNA, cDNA, DNA-RNA hybrids, or a polymer comprising purine and pyrimidine bases or other natural, chemically or biochemically modified, non-natural, or derivatized nucleotide bases. The backbone of the polynucleotide can comprise sugars and phosphate groups (as may typically be found in RNA or DNA), or modified or substituted sugar or phosphate groups. Alternatively, the backbone of the polynucleotide can comprise a polymer of synthetic subunits such as phosphoramidites, and/or phosphorothioates, and thus can be an oligodeoxynucleoside phosphoramidate or a mixed phosphoramidate-phosphodiester oligomer. Peyrottes et al. (1996) *Nucl. Acids Res.* 24:1841–1848; Chaturvedi et al. (1996) *Nucl. Acids Res.* 24:2318–2323. The polynucleotide may comprise one or more L-nucleosides. A polynucleotide may comprise modified nucleotides, such as methylated nucleotides and nucleotide analogs, uracyl, other sugars, and linking groups such as fluororibose and thioate, and nucleotide branches. The sequence of nucleotides may be interrupted by non-nucleotide components. A polynucleotide may be further modified after polymerization, such as by conjugation with a labeling component. Other types of modifications included in this definition are caps, substitution of one or more of the naturally occurring nucleotides with an analog, and introduction of means for attaching the polynucleotide to proteins, metal ions, labeling components, other polynucleotides, or a solid support.

The terms "polypeptide," "peptide," and "protein", used interchangeably herein, refer to a polymeric form of amino acids of any length, which can include coded and non-coded amino acids, chemically or biochemically modified or derivatized amino acids, and polypeptides having modified peptide backbones. The term includes polypeptide chains modified or derivatized in any manner, including, but not limited to, glycosylation, formylation, cyclization, acetylation, phosphorylation, and the like. The term includes naturally-occurring peptides, synthetic peptides, and peptides comprising one or more amino acid analogs. The term includes fusion proteins, including, but not limited to, fusion proteins with a heterologous amino acid sequence, fusions with heterologous and homologous leader sequences, with or without N-terminal methionine residues; immunologically tagged proteins; and the like.

The term "tumor-associated antigen" is a term well understood in the art, and refers to surface molecules that are differentially expressed in tumor cells relative to non-cancerous cells of the same cell type. As used herein, "tumor-associated antigen" includes not only complete tumor-associated antigens, but also epitope-comprising portions (fragments) thereof. A tumor-associated antigen (TAA) may be one found in nature, or may be a synthetic version of a TAA found in nature, or may be a variant of a naturally-occurring TAA, e.g., a variant which has enhanced immunogenic properties.

"A peptide associated with a pathogenic organism," as used herein, is a peptide (or fragment or analog thereof) that is normally a part of a pathogenic organism, or is produced by a pathogenic organism. Generally, a peptide associated with a pathogenic organism is one that is recognized as foreign by a normal individual with a healthy, intact immune system, e.g., the peptide is displayed together with an MHC Class I molecule on the surface of a cell, where it is recognized by a $CD8^+$ lymphocyte.

The terms "antigen" and "epitope" are well understood in the art and refer to the portion of a macromolecule which is specifically recognized by a component of the immune system, e.g., an antibody or a T-cell antigen receptor. As used herein, the term "antigen" encompasses antigenic epitopes, e.g., fragments of an antigen which are antigenic epitopes. Epitopes are recognized by antibodies in solution, e.g. free from other molecules. Epitopes are recognized by T-cell antigen receptor when the epitope is associated with a class I or class II major histocompatibility complex molecule.

The terms "preventing," "reducing," and "inhibiting," used interchangeably herein in the context of pathogen infection refer to reducing the incidence of pathogen infection of a cell which is susceptible to infection by the pathogen. Reducing pathogen infection refers to reducing any parameter or event which leads to pathogen entry into a cell, including, but not limited to, reducing co-receptor-mediated fusion; reducing entry of the pathogen into the cell; reducing binding of the pathogen to a cell-surface chemokine receptor; and reducing binding of the pathogen to a cell-surface CD4 molecule. The terms also refer to reducing susceptibility of a cell to infection by a pathogen. The terms also refer to reducing any undesired effect of binding of a pathogen to the cell. As used herein, "a cell which is susceptible to infection by a pathogen" is a cell which can be infected by a pathogen that establishes infection or otherwise causes disease or symptoms of disease in a host by interaction with a chemokine receptor.

As used herein the term "isolated" is meant to describe a compound of interest (e.g., a virus, a peptide, etc.) that is in an environment different from that in which the compound naturally occurs. "Isolated" is meant to include compounds that are within samples that are substantially enriched for the compound of interest and/or in which the compound of interest is partially or substantially purified.

As used herein, the term "substantially purified" refers to a compound that is removed from its natural environment and is at least 60% free, preferably 75% free, and most preferably 90% free from other components with which it is naturally associated.

The terms "immunomodulatory nucleic acid molecule," "immunostimulatory nucleic acid molecule," "ISS," "ISS-PN," and "ISS-ODN," are used interchangeably herein to refer to a polynucleotide that comprises at least one immunomodulatory nucleic acid moiety. The terms "immunomodulatory," and "immunostimulatory," as used herein in reference to a nucleic acid molecule, refer to the ability of a nucleic acid molecule to modulate an immune response in a vertebrate host. In particular, these terms refer to the ability of an immunostimulatory nucleic acid molecule to increase an immune response in a vertebrate host, particularly to increase a CTL response, particularly an antigen-specific CTL response.

The terms, "increasing," "inducing," and "enhancing," used interchangeably herein with reference to a CTL response, refer to any increase in a CTL response over background, and include inducing a CTL response over an absence of a measurable CTL response, or increasing CTL response over a previously measurable CTL response.

The terms "$CD4^+$-deficient" and "$CD4^+$-low" are used interchangeably herein, and, as used herein, refer to a state of an individual in whom the number of $CD4^+$ T lymphocytes is reduced compared to an individual with a healthy, intact immune system. $CD4^+$ deficiency includes a state in which the number of functional CD4$^+$ T lymphocytes is less than about 600 CD4$^+$ T cells/mm$^3$ blood; a state in which the number of functional CD4$^+$ T cells is reduced compared to a healthy, normal state for a given individual; and a state in which functional CD4$^+$ T cells are completely absent.

As used herein, a "CD4$^+$-deficient individual" is one who has a reduced number of functional CD4$^+$-T cells, regardless of the reason, when compared to an individual having a normal, intact immune system. In general, the number of functional CD4$^+$-T cells that is within a normal range is known for various mammalian species. In human blood, e.g., the number of functional CD4$^+$-T cells which is considered to be in a normal range is from about 600 to about 1500 CD4$^+$-T cells/mm$^3$ blood. An individual having a number of CD4$^+$-T cells below the normal range, e.g., below about 600/mm$^3$, may be considered "CD4$^+$-deficient." Thus, a CD4$^+$-deficient individual may have a low CD4$^+$ T cell count, or even no detectable CD4$^+$ cells. A CD4$^+$-deficient individual includes an individual who has a lower than normal number of functional CD4$^+$-T cells due to a primary or an acquired immunodeficiency.

A "functional CD4$^+$-T cell" is a term well understood in the art and refers to a CD4$^+$-T cell which is capable of providing T cell help, directly or indirectly, to effect one or more of the following responses: CTL activation; antibody production; macrophage activation; mast cell growth; and eosinophil growth and differentiation.

As used herein, the terms "immunodeficient," "immunosuppressed," and "immunocompromised," used interchangeably herein, refer to a state of a CD4$^+$-deficient individual.

As used herein, the term "soluble exogenous antigen" refers to an antigen that a cell takes up from its environment, and processes intracellularly. A "soluble exogenous antigen" is distinguished from an antigen that is synthesized intracellularly (e.g., translated in the cell cytoplasm).

As used herein, the terms "treatment", "treating", and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse affect attributable to the disease. "Treatment", as used herein, covers any treatment of a disease in a mammal, particularly in a human, and includes: (a) preventing the disease from occurring in a subject which may be predisposed to the disease but has not yet been diagnosed as having it; (b) inhibiting the disease, i.e., arresting its development; and (c) relieving the disease, e.g., causing regression of the disease, e.g., to completely or partially remove symptoms of the disease.

The term "biological sample" encompasses a variety of sample types obtained from an organism and can be used in a diagnostic or monitoring assay. The term encompasses blood and other liquid samples of biological origin, solid tissue samples, such as a biopsy specimen or tissue cultures or cells derived therefrom and the progeny thereof. The term encompasses samples that have been manipulated in any way after their procurement, such as by treatment with reagents, solubilization, or enrichment for certain components. The term encompasses a clinical sample, and also includes cells in cell culture, cell supernatants, cell lysates, serum, plasma, biological fluids, and tissue samples.

The terms "cancer", "neoplasm", "tumor", and "carcinoma", are used interchangeably herein to refer to cells which exhibit relatively autonomous growth, so that they exhibit an aberrant growth phenotype characterized by a significant loss of control of cell proliferation. Cancerous cells can be benign or malignant.

By "individual" or "host" or "subject" or "patient" is meant any mammalian subject for whom diagnosis, treatment, or therapy is desired, particularly humans. Other subjects may include cattle, dogs, cats, guinea pigs, rabbits, rats, mice, horses, and so on.

Methods of Increasing an Antigen-Specific CTL Response in Vivo

The invention provides methods for induction of a CTL response to any exogenous soluble antigen via a process of cross-presentation. In addition, the invention provides methods for T helper-independent activation of an antigen-specific cytotoxic T lymphocyte response in an individual; methods for decreasing the number of infectious pathogens in an individual; methods for decreasing tumor load in an individual; and methods of treating an infectious disease in an individual. The methods generally involve administering to an individual an immunostimulatory nucleic acid molecule (either alone or in combination with one or more antigens) in an amount effective to increase an antigen-specific CTL response in the individual and/or to decrease a tumor load in an individual and/or to prevent and/or reduce an infectious disease in an individual.

During an immune response, an antigen presenting cell (APC) presents antigen to T lymphocytes, and the result may be production of antigen-specific antibody, and activation of antigen-specific cytotoxic cells which serve to destroy cells displaying foreign antigen on their cell surface. It was previously believed that CD4$^+$ cells were required for CTL activation. Without wishing to be bound by theory, immunostimulatory nucleic acid molecules may bypass the requirement for CD4$^+$ cells, and may induce APC's to activate a CTL response directly, even in the absence of CD4$^+$ cells, or in the presence of an insufficient number of functional CD4$^+$ cells. The present invention provides a means for increasing antigen-specific CTL activity even in the absence of CD4$^+$ cells.

The results presented in the Examples also demonstrate that an immunostimulatory nucleic acid molecule can, when administered together with a soluble exogenous antigen, increase both an antigen-specific CTL response to the soluble antigen and cross-reacting epitopes, as well as an antigen-specific humoral response to the soluble antigen and cross-reacting epitopes.

T lymphocytes capable of antigen recognition are generally classified as "CD4$^+$" or "CD8$^+$," depending on whether a CD4 or a CD8 molecule is displayed on the cell surface. CD4$^+$ cells recognize exogenously-produced antigen which has been taken up by an antigen presenting cell (APC), processed, and displayed on the APC cell surface together with a major histocompatibility complex (MHC) class II molecule. In general, CD4$^+$ T cells provide the signals to activate other cells, e.g., CD4$^+$ cells activate CD8$^+$ cells, to induce B cell to produce antibodies, or to activate macrophages. In contrast, CD8$^+$ cells are cytotoxic, and recognize antigen produced from within a cell and displayed on the cell surface together with an MHC Class I molecule.

In general, CD4$^+$ helper T (Th) cells are divided into broad groups based on their specific profiles of cytokine production: Th1, Th2, and Th0. "Th1" cells are T lymphocytes that release predominantly the cytokines IL-2 and IFN-$\gamma$, which cytokines in turn promote T cell proliferation, facilitate macrophage activation, and enhance the cytolytic activity of natural killer (NK) cells and antigen-specific cytotoxic T cells (CTL). In contrast, the cytokines predominantly released by Th2 cells are IL-4, IL-5, and IL-10. IL-4 and IL-5 are known to mediate antibody isotype switching towards IgE or IgA response, and promote eosinophil recruitment, skewing the immune system toward an "allergic" type of response. Th0 cells release a set of cytokines with characteristics of both Th1-type and Th2-type responses. While the categorization of T cells as Th1, Th2, or Th0 is helpful in describing the differences in immune response, it should be understood that it is more accurate to view the T cells and the responses they mediate as forming a continuum, with Th1 and Th2 cells at opposite ends of the scale, and Th0 cells providing the middle of the spectrum. Therefore, it should be understood that the use of these terms herein is only to describe the predominant nature of the immune response elicited, and is not meant to be limiting to an immune response that is only of the type indicated. Thus, for example, reference to a "type-1" or "Th1" immune response is not meant to exclude the presence of a "type-2" or "Th2" immune response, and vice versa.

The immunostimulatory nucleic acid molecule may be administered before, simultaneously with (e.g., in admixture with antigen, or covalently or non-covalently bound, directly or via a linker, to an antigen or antigenic epitope), or after the subject is exposed to antigen. Exposure to antigen may occur by intentionally introducing the antigen into the subject via a systemic or mucosal route, e.g., intranasally, intrarectally, intravenously, subcutaneously, intradermally, or intraperitoneally, and the like, e.g., by a clinician. Alternatively, exposure to antigen may occur accidentally or naturally (e.g., by happenstance), e.g., by the usual routes of exposure of a subject to plant, animal, and other antigens, such as by inhalation, accidental skin exposure, ingestion, and the like.

Methods of T helper-independent Activation of an Antigen-specific CTL Response

The present invention provides methods of increasing an antigen-specific CTL response in an individual, comprising administering a formulation comprising an immunostimulatory nucleic acid molecule to the individual.

An antigen-specific CTL response may be directed to an intracellular pathogen, such as a virus, an intracellular bacterium, fungus, or protozoan; or may be directed to a tumor-associated antigen. Pathogens include microorganisms that are commonly pathogenic in healthy individuals with an intact immune system, as well as microorganisms that cause opportunistic infections in individuals who are immunocompromised.

In general, the methods for increasing an antigen-specific CTL response are effective to increase an antigen-specific CTL response by at least about 10%, at least about 20%, at least about 25%, at least about 50%, at least about 75%, at least about 100% (or two-fold), at least about 5-fold, at least about 10-fold, at least about 20-fold, at least about 50-fold, or at least about 100-fold or more, when compared to a suitable control. Thus, in these embodiments, an "effective amount" of an immunostimulatory nucleic acid molecule is an amount sufficient to increase an antigen-specific CTL response in an individual by at least about 10%, at least about 20%, at least about 25%, at least about 50%, at least about 75%, at least about 100% (or two-fold), at least about 5-fold, at least about 10-fold, at least about 20-fold, at least about 50-fold, or at least about 100-fold or more, when compared to a suitable control. In an experimental animal system, a suitable control may be a genetically identical animal not treated with the immunostimulatory nucleic acid molecule. In non-experimental systems, a suitable control may be the level of antigen-specific CTL present before administering the immunostimulatory nucleic acid molecule. Other suitable controls may be a placebo control.

In some embodiments, an immunostimulatory nucleic acid molecule is co-administered with a soluble exogenous antigen. In certain embodiments, the immunostimulatory nucleic acid molecule and soluble exogenous antigen are admixed with one another; in certain other embodiments, the immunostimulatory nucleic acid molecule and soluble exogenous antigen are linked to one another (e.g., either covalently or non-covalently, e.g., to place the antigen and the immunostimulatory nucleic acid molecule in spatial proximity at a distance sufficient to provide for the desired immunomodulatory effect). Co-administration of an immunostimulatory nucleic acid molecule and a soluble exogenous antigen results in an increase in both antigen-specific CTL response and antigen-specific humoral response. An antigen-specific CTL response to a soluble exogenous antigen encompasses a CTL response to an epitope that is shared between the soluble exogenous antigen and another protein.

Whether an antigen-specific CTL response is increased can be determined using any of a number of assays known in the art, including, but not limited to, measuring specific lysis by CTL of target cells expressing antigen on their surface, which target cells have incorporated a detectable label which is released from target cells upon lysis, and can be measured, using, e.g., an assay such as that described in the Examples, a $^{51}$Cr-release assay, a lanthanide fluorescence-based cytolysis assay, and the like.

An immunostimulatory nucleic acid molecule can also elicit production of IFNγ in CD4-deficient individuals. Thus, in some embodiments, the invention provides methods of increasing IFNγ production in a CD4+ T cell deficient individual, comprising administering a formulation comprising an immunostimulatory nucleic acid molecule to the individual. In many embodiments, an immunostimulatory nucleic acid molecule is administered together with (e.g., in admixture, as a conjugate, etc.) an antigen. In these embodiments, IFNγ is produced in an antigen-specific manner, e.g., IFNγ is produced in response to the antigen administered, to an epitope contained on the administered antigen, or to a cross-reactive antigen or epitope, but not to an unrelated antigen. IFNγ is produced in an antigen-specific manner by $CD8^+$ cells in $CD4^+$-deficient individuals. In the context of IFNγ production, an "effective amount" of an immunostimulatory nucleic acid molecule is an amount sufficient to increase production of IFNγ in an individual by at least about 10%, at least about 20%, at least about 25%, at least about 50%, at least about 75%, at least about 100% (or two-fold), at least about 5-fold, at least about 10-fold, at least about 20-fold, at least about 50-fold, or at least about 100-fold or more, when compared to a suitable control, as described above.

Whether IFNγ production is increased can be determined using any known assay. A non-limiting example of such an assay is an enzyme-linked immunosorbent assay, using antibody specific for IFNγ.

Methods of Decreasing Tumor Load in an Individual

The present invention further provides methods for decreasing tumor load in an individual, comprising administering a formulation comprising an immunostimulatory nucleic acid molecule to the individual, in an amount effective to reduce the tumor load.

The methods are effective to reduce a tumor load by at least about 5%, at least about 10%, at least about 20%, at least about 25%, at least about 50%, at least about 75%, at least about 85%, or at least about 90%, up to total eradication of the tumor, when compared to a suitable control. Thus, in these embodiments, an "effective amount" of an immunostimulatory nucleic acid molecule is an amount sufficient to reduce a tumor load by at least about 5%, at least about 10%, at least about 20%, at least about 25%, at least about 50%, at least about 75%, at least about 85%, or at least about 90%, up to total eradication of the tumor, when compared to a suitable control. In an experimental animal system, a suitable control may be a genetically identical animal not treated with the immunostimulatory nucleic acid molecule. In non-experimental systems, a suitable control may be the tumor load present before administering the immunostimulatory nucleic acid molecule. Other suitable controls may be a placebo control.

Whether a tumor load has been decreased can be determined using any known method, including, but not limited to, measuring solid tumor mass; counting the number of tumor cells using cytological assays; fluorescence-activated cell sorting (e.g., using antibody specific for a tumor-associated antigen); computed tomography scanning, magnetic resonance imaging, and/or x-ray imaging of the tumor to estimate and/or monitor tumor size; measuring the amount of tumor-associated antigen in a biological sample, e.g., blood; and the like.

Methods of Preventing or Treating an Infectious Disease in an Individual

The present invention further provides methods for preventing or treating an infectious disease in an individual, comprising administering a formulation comprising an immunostimulatory nucleic acid molecule to the individual, in an amount effective to prevent or treat the disease. The methods are particularly useful for preventing or treating infectious diseases caused by intracellular pathogens, such as viruses, intracellular bacteria, fungi and parasites (e.g. protozoans). In particular, opportunistic infections can be treated using the methods of the invention.

"Preventing an infectious disease," as used herein, refers to reducing the likelihood that an individual, upon infection by a pathogenic organism, will exhibit the usual symptoms of a disease caused by a pathogenic organism.

"Treating an infectious disease," as used herein, encompasses reducing the number of pathogenic agents in the individual (e.g., reducing viral load) and/or reducing a parameter associated with the infectious disease, including, but not limited to, reduction of a level of a product produced by the infectious agent (e.g., a toxin, an antigen, and the like); and reducing an undesired physiological response to the infectious agent (e.g., fever, tissue edema, and the like).

The methods are effective to treat an infectious disease by at least about 5%, at least about 10%, at least about 20%, at least about 25%, at least about 50%, at least about 75%, at least about 85%, or at least about 90%, up to total eradication of the infecting pathogen and/or an associated parameter, when compared to a suitable control. Thus, in these embodiments, an "effective amount" of an immunostimulatory nucleic acid molecule is an amount sufficient to treat an infectious disease, e.g., to reduce the number of pathogens and/or reduce a parameter associated with the presence of a pathogen, by at least about 5%, at least about 10%, at least about 20%, at least about 25%, at least about 50%, at least about 75%, at least about 85%, or at least about 90%, up to total eradication of the infectious disease, when compared to a suitable control. In an experimental animal system, a suitable control may be a genetically identical animal not treated with the immunostimulatory nucleic acid molecule. In non-experimental systems, a suitable control may be the infectious disease present before administering the immunostimulatory nucleic acid molecule. Other suitable controls may be a placebo control.

Whether an infectious disease has been treated can be determined in any of a number of ways, including but not limited to, measuring the number of infectious agents in the individual being treated, using methods standard in the art; measuring a parameter caused by the presence of the pathogen in the individual, e.g., measuring the levels of a toxin produced by the pathogen; measuring body temperature; measuring the level of any product produced by the pathogen; measuring or assessing any undesired physiological parameter associated with the presence of an infectious agent in an individual. Measuring the number of infectious agents can be accomplished by any conventional assay, such as those typically used in clinical laboratories, for evaluating numbers of pathogens present in a biological sample obtained from an individual. Such methods have been amply described in the literature, including, e.g., *Medical Microbiology* 3rd Ed., (1998) P. R. Murray et al., eds. Mosby-Year Book, Inc. A level of a product, including a toxin, produced by a pathogen can be measured using conventional immunological assays, using antibody which detects the product, including, but not limited to enzyme-linked immunosorbent assays (ELISA), radioimmunoassays. Other assays, include in vivo assays for toxins.

Subjects Suitable for Treatment with the Methods of the Invention

Subjects suitable for treatment with the methods of the invention include an individual who has been infected with a pathogenic microorganism; an individual who is susceptible to infection by a pathogenic microorganism, but who has not yet been infected; and an individual who has a tumor.

Subjects particularly suitable for treatment with the methods of the invention include $CD4^+$-deficient individuals, e.g., individuals who have lower than normal numbers of functional $CD4^+$ T lymphocytes. As used herein, the term "normal individual" refers to an individual having $CD4^+$ T lymphocyte levels and function(s) within the normal range in the population, for humans, typically 600 to 1500 $CD4^+$ T lymphocytes per $mm^3$ blood. $CD4^+$-deficient individuals individuals who have an acquired immunodeficiency, or a primary immunodeficiency. An acquired immunodeficiency may be a temporary $CD4^+$ deficiency, such as one caused by radiation therapy, or chemotherapy, as described below.

Also suitable for treatment with the methods of the invention are individuals with healthy, intact immune systems, but who are at risk for becoming $CD4^+$ deficient ("at-risk" individuals). At-risk individuals include, but are not limited to, individuals who have a greater likelihood than the general population of becoming $CD4^+$ deficient. Individuals at risk for becoming $CD4^+$ deficient include, but are not limited to, individuals at risk for HIV infection due to sexual activity with HIV-infected individuals; intravenous drug users; individuals who may have been exposed to HIV-infected blood, blood products, or other HIV-contaminated body fluids; babies who are being nursed by HIV-infected mothers; individuals who were previously treated for cancer, e.g., by chemotherapy or radiotherapy, and who are being monitored for recurrence of the cancer for which they were previously treated; and individuals who have undergone bone marrow transplantation or any other organ transplantation.

A reduction of normal levels and/or function of $CD4^+$ T lymphocytes compared to a normal individual can result from a variety of disorders, diseases infections or conditions, including immunosuppressed conditions due to leukemia, renal failure; autoimmune disorders, including, but not limited to, systemic lupus erythematosus, rheumatoid arthritis, auto-immune thyroiditis, scleroderma, inflammatory bowel disease; various cancers and tumors; viral infections, including, but not limited to, human immunodeficiency virus (HIV); bacterial infections; and parasitic infections.

A reduction of normal levels and/or function of CD4+ T lymphocytes compared to a normal individual can also result from an immundeficiency disease or disorder of genetic origin, or due to aging. Examples of these are immunodeficiency diseases associated with aging and those of genetic origin, including, but not limited to, hyperimmunoglobulin M syndrome, CD40 ligand deficiency, IL-2 receptor deficiency, γ-chain deficiency, common variable immunodeficiency, Chediak-Higashi syndrome, and Wiskott-Aldrich syndrome.

A reduction of normal levels and/or function of CD4+ T lymphocytes compared to a normal individual can also result from treatment with specific pharmacological agents, including, but not limited to chemotherapeutic agents to treat cancer; certain immunotherapeutic agents; radiation therapy; immunosuppressive agents used in conjunction with bone marrow transplantation; and immunosuppressive agents used in conjunction with organ transplantation.

Accordingly, individuals who may benefit from treatment using the methods of the present invention include, but are not limited to, individuals with various cancers, including, but not limited to, leukemia, Hodgkin's disease, lung cancer, colon cancer, gliomas, renal cell carcinoma, etc.; individuals with various bacterial, protozoan, and viral infections, including, but not limited to, patients with acquired immunodeficiency syndrome (AIDS), cytomegalovirus infections, malaria, Epstein Barr Virus, etc.; individuals infected with intracellular pathogens, including, but not limited to, individuals with leprosy, tuberculosis, leishmania; individuals with autoimmune diseases, including, but not limited to systemic lupus erythematosus, rheumatoid arthritis, scleroderma, autoimmune thyroiditis; and individuals who have undergone stem cell replacement therapy, organ transplantation, bone marrow transplant, chemotherapy, radiotherapy and the like.

Methods of Increasing Chemokine Secretion

The present invention provides methods for increasing chemokine production and secretion by a cell. The methods are useful for treating various disorders which are mediated by cells expressing chemokine receptors. In some embodiments, the methods are carried out in vitro or ex vivo. In these embodiments, the methods generally involve contacting the cell with an immunostimulatory nucleic acid molecule in an amount sufficient to increase secretion of a chemokine. In other embodiments, the methods are carried out in vivo. In these embodiments, the methods generally involve administering to an individual an immunostimulatory nucleic acid molecule in an amount sufficient to increase secretion of a chemokine. In some embodiments, the invention provides methods for increasing chemokine production and secretion in an antigen non-specific manner. In these embodiments, cells are contacted with, or individuals are administered with, immunostimulatory nucleic acid molecule without antigen. In other embodiments, the invention provides methods for increasing chemokine production and secretion in an antigen-specific manner. In these embodiments, immunostimulatory nucleic acid molecule and antigen are brought into contact with cells, or administered to an individual.

The methods of the invention increase secretion of a chemokine from a cell that normally produces a chemokine, particularly those cells that are susceptible to infection by a pathogen. Cells that normally produce chemokines include, but are not limited to, T lymphocytes, macrophages, monocytes, dendritic cells and related antigen-presenting cells (APCs), B lymphocytes, epithelial cells, fibroblasts, endothelial cells, basophils, eosinophils, neutrophils, natural killer cells, and bone marrow stem cells.

Chemokines whose secretion is increased by contacting a cell that normally produces a chemokine with an immunostimulatory nucleic acid molecule include, but are not limited to, MIP-1α, and MIP-1β. Other chemokines which may have increased secretion in response to immunostimulatory nucleic acid include, but are not necessarily limited to, RANTES, SDF-1, MCP-1, MCP-2, MCP-3, MCP-4, eotaxin, eotaxin-2,I-309/TCA3, ATAC, HCC-1, HCC-2, HCC-3, LARC/MIP-3α, PARC, TARC, CKβ4, CKβ6, CKβ7, CKβ8, CKβ9, CKβ11, CKβ12, and CKβ13, C10, an interleukin-8 (IL-8) family member; GROα, GROβ, GROγ, mouse KC, mouse MIP-2, ENA-78, GCP-2, PBP/CTAPIII/ β-TG/NAP-2, IP-10/mouse CRG, Mig, PBSF/SDF-1, a member of the platelet factor 4 (PF4) family, lymphotactin, or an equivalent in any mammalian species of any of the foregoing.

In some embodiments, the cells are susceptible to infection with a pathogen that exploits a chemokine receptor to establish infection and/or cause disease symptoms, e.g., an immunodeficiency virus. In some of these embodiments, the cells are macrophages and/or monocytes and/or T cells. In particular embodiments, the cells are macrophages and/or monocytes, and/or T lymphocytes, and the chemokines are MIP-1α, and/or MIP-1β, and/or RANTES.

In some embodiments, methods are provided for increasing chemokine secretion in an antigen non-specific manner. In these embodiments, an immunostimulatory nucleic acid molecule is brought into contact with a cell, or administered to an individual, in the absence of exogenously provided antigen, i.e., antigen is not intentionally introduced into the individual, either before, simultaneously with, or after introduction of the immunostimulatory nucleic acid molecule into the individual.

In particular embodiments, production and secretion of a chemokine is antigen-specific. The term "antigen-specific" is one well understood in the art, and refers to chemokine production in response to the antigen with which the individual is immunized, or to closely related ("cross-reactive") antigens, e.g., antigens that share one or more epitopes with the immunizing antigen. In in vivo embodiments, the method generally involves administering to an individual an immunostimulatory nucleic acid molecule and an antigen, wherein the immunostimulatory nucleic acid molecule is administered in an amount sufficient to increase secretion of a chemokine in an antigen-specific manner. In in vitro or ex vivo embodiments, the method generally involves contacting a cell with an immunostimulatory nucleic acid molecule and an antigen, wherein the cell is contacted with immunostimulatory in an amount sufficient to increase secretion of a chemokine in an antigen-specific manner.

The immunostimulatory nucleic acid molecule and the antigen may be administered substantially simultaneously, or the immunostimulatory nucleic acid molecule may be administered before or after the antigen. Generally, the immunostimulatory nucleic acid molecule and the antigen are administered within about 72 hours, about 48 hours, about 24 hours, about 12 hours, about 8 hours, about 4 hours, about 2 hours, about I hour, or about 30 minutes or less, of each other.

Antigen may be administered separately from the immunostimulatory nucleic acid molecule, in admixture with immunostimulatory nucleic acid molecule, or the immunostimulatory nucleic acid and antigen can be proximately associated with (e.g., conjugated or brought into spatial proximity by other means, as described in more detail below) to one or more immunostimulatory nucleic acid molecules. Generally, and most preferably, an immunomodulatory nucleic acid and an antigen are proximately associated at a distance effective to enhance the immune response generated compared to the administration of the ISS and antigen as an admixture. For a detailed discussion of method for proximate association of a polynucleotide and an antigen see, e.g., PCT Publication WO 00/21556, incorporated herein by reference.

Whether chemokine secretion is increased in an antigen-specific manner can be readily determined by those skilled in the art using standard methods. As one non-limiting example, splenocytes from an individual immunized with immunostimulatory nucleic acid molecule plus antigen are cultured in the presence of the immunizing antigen, and secretion of chemokines measured using any known method, as described below.

In vitro and ex vivo methods of the invention comprise contacting a cell that normally produces a chemokine with an immunostimulatory nucleic acid molecule. In these embodiments, contacting a cell that normally produces a chemokine with an immunostimulatory nucleic acid molecule increases chemokine secretion from the cell by at least about 10%, at least about 25%, at least about 30%, at least about 50%, at least about 75%, at least about 100% (or two-fold), at least about five fold, at least about 10 fold, at least about 15 fold, at least about 25 fold, at least about 50 fold, at least about 75 fold, at least about 100 fold, at least about 200 fold, at least about 300 fold, at least about 400 fold, at least about 500 fold, at least about 600 fold, at least about 700 fold, at least about 800 fold, at least about 900 fold, at least about 1000 fold, at least about 2000 fold, at least about 3000 fold, at least about 4000 fold, at least about 5000 fold, or at least about 10,000 fold or more, when compared the level of secretion of the chemokine from the cell not contacted with the immunostimulatory nucleic acid molecule.

In vivo methods of the invention comprise administering to an individual an immunostimulatory nucleic acid molecule in an amount sufficient to increase secretion of a chemokine from a cell that normally produces a chemokine. A "sufficient amount," used interchangeably in this context with "an effective amount," is an amount of immunostimulatory nucleic acid molecule sufficient to increase chemokine secretion such that the level of chemokine produced is increased by at least about 10%, at least about 25%, at least about 30%, at least about 50%, at least about 75%, at least about 100% (or two-fold), at least about five fold, at least about 10 fold, at least about 15 fold, at least about 25 fold, at least about 50 fold, at least about 75 fold, at least about 100 fold, at least about 200 fold, at least about 300 fold, at least about 400 fold, at least about 500 fold, at least about 600 fold, at least about 700 fold, at least about 800 fold, at least about 900 fold, at least about 1000 fold, at least about 2000 fold, at least about 3000 fold, at least about 4000 fold, at least about 5000 fold, or at least about 10,000 fold or more, when compared the level of chemokine in the individual before being administered with the immunostimulatory nucleic acid molecule.

Whether, and to what extent, an immunostimulatory nucleic acid molecule increases chemokine secretion from a cell that normally produces (e.g., is capable of producing) can be readily determined using any known assay method. The amount of chemokine secreted from a cell can be determined quantitatively (e.g., the amount secreted measured) or semi-quantitatively (e.g., the amount secreted relative to a control determined). Levels of chemokine can be determined using any method known in the art, including a biochemical assay, an immunological assay, or a biological assay. Immunological assays include, but are not limited to, radioimmunoassays, and enzyme-linked immunosorbent assays (ELISA), a number of which are commercially available. Assays can be conducted in vitro, e.g., by adding an immunostimulatory nucleic acid molecule to the cell culture medium of an in vitro cell culture, and, after a suitable time (e.g., about 10 minutes to about 24 hours), determining the level of chemokine in the cell culture supernatant.

Biological assays include, but are not limited to, in vitro assays to detect pathogen binding to and/or entry into a cell bearing a chemokine receptor on its surface, which receptor serves as a receptor or co-receptor for infection by the pathogen or as a receptor or co-receptor for a pathogen-derived ligand that elicits disease symptoms or causes disease. Any known assay to determine infection of a cell with a pathogen can be used. For example, binding or infection by an immunodeficiency virus can be detected by syncitia formation, cytopathic effects, production of an immunodeficiency virus-encoded polypeptide, e.g. p24, and/or reverse transcriptase, and/or gp120.

As one non-limiting example, the following protocol can be used. Peripheral blood mononuclear cells (PBMC) cultures are infected with a virus stock. Virus is harvested when p24 or reverse transcriptase (RT) is detected in the supernatant. Dilutions of a solution (e.g., a cell culture supernatant) are mixed with target phytohemagglutinin- (PHA-) and IL-2-stimulated PBMCs and incubated at 37° C. for 30 minutes, and are then exposed to an equal volume of virus supernatant containing 1000 times the median tissue culture infectious dose (TCID50), and reincubated at 37° C. for 3 hours. Input virus is then washed out before adding growth medium containing appropriate chemokine concentrations. The cultures are incubated at 37 C. for up to 12 days with medium changes twice weekly but without further addition of chemokine. Virus production into the supernatant is assessed by measurement of RT activity using a sensitive nonradioactive method (e.g., a commercially available assay, e.g., the Retrosys RT activity kit from Innovagen AB, Lund, Sweden). Simmons et al. (1997) *Science* 276:276–279.

Disorders Amenable to Treatment by the Methods of the Invention

Diseases

Diseases or conditions of humans or other mammals which are amenable to treatment by increasing chemokine secretion include, but are not limited to, immunosuppression, such as that in individuals with immunodeficiency syndromes such as acquired immunodeficiency syndrome (AIDS); infection by an immunodeficiency virus, including, but not limited to human immunodeficiency virus (HIV) (including any known subtype), simian immunodeficiency virus, and feline immunodeficiency virus; radiation therapy, chemotherapy, immunosuppressive therapy for an autoimmune disease, or other drug therapy which causes immunosuppression; immunosuppression due to congenital deficiency in receptor function or other causes; chronic infectious diseases, including, but not limited to, hepatitis B and hepatitis C infections; and infectious diseases, such as parasitic diseases, including but not limited to, leshmaniasis, helminth infections, such as nematodes, trematodes, cestodes, visceral worms, visceral larva migrans, and the like.

Methods of Reducing Entry of a Pathogen into a Cell

The present invention further provides methods for reducing entry of a pathogen, e.g., an immunodeficiency virus, into a cell. The methods generally involve contacting the cell with an immunostimulatory nucleic acid molecule. The methods are useful for reducing infection with an immunodeficiency virus in an individual.

In the context of methods of reducing pathogen entry into a susceptible cell, an effective amount of an immunostimulatory nucleic acid molecule is one that increases chemokine secretion from a cell and reduces infection by the pathogen into the same cell or cells in the vicinity of the chemokine-producing cell. The cell secreting chemokine and the cell susceptible to infection by the pathogen may be the same cell, but need not be.

As used herein, "reducing pathogen entry into a cell susceptible to pathogen infection" encompasses reducing pathogen entry into a cell susceptible to pathogen infection, reducing pathogen binding to a cell susceptible to pathogen infection. In this context, the terms "reducing" and "inhibiting" and "preventing" are used interchangeably herein.

Methods of the invention for reducing pathogen entry into a cell susceptible to pathogen infection are also useful for treating a pathogen infection. "Treating a pathogen infection," as used herein, includes, but is not limited to, preventing an infection in an individual who does not yet have a clinically detectable infection; reducing the probability of an infection in an individual who does not yet have a clinically detectable infection; reducing spread of pathogen from an infected cell to a cell not yet infected but susceptible to infection; improving one or more indicia of an infection. For example, treating an HIV infection, includes, but is not limited to, preventing HIV infection, reducing the probability of HIV infection, reducing the spread of HIV from an infected cell to a susceptible cell, reducing viral load in an HIV-infected individual, reducing an amount of virally-encoded polypeptide(s) in an HIV-infected individual, and increasing CD4 T cell count in an HIV-infected individual.

Methods of determining whether the methods of the invention are effective in reducing pathogen-induced disease in a susceptible cell include any known test for infection by a given pathogen, including, but not limited to, measuring the number of pathogens in a biological sample from a host, e.g., by using a PCR with primers specific for a nucleotide sequence in the pathogen; counting the number of pathogens in the host; detecting or measuring a polypeptide or other product produced by the pathogen; and measuring an indicia of pathogen infection.

For example, methods of determining whether the methods of the invention are effective in reducing HIV entry into a cell, and/or treating an HIV infection, are any known test for indicia of HIV infection, including, but not limited to, measuring viral load, e.g., by measuring the amount of HIV in a biological sample, e.g., using a polymerase chain reaction (PCR) with primers specific for an HIV polynucleotide sequence; detecting and/or measuring a polypeptide encoded by HIV, e.g., p24, gp120, reverse transcriptase, using, e.g., an immunological assay with an antibody specific for the polypeptide; and measuring CD4 cell count in the individual. Methods of assaying an HIV infection (or any indicia associated with an HIV infection) are known in the art, and have been described in numerous publications such as *HIV Protocols (Methods in Molecular Medicine,* 17) N. L. Michael and J. H. Kim, eds. (1999) Humana Press.

Subjects suitable for treatment with the methods of the invention include, but are not limited to, individuals infected with a pathogen; and individuals not yet infected with the pathogen, but at risk for becoming infected. For example, subjects suitable for treatment with the methods of the invention include, but are not limited to, individuals who have been diagnosed as having an HIV infection; individuals at risk for HIV infection due to sexual activity with HIV-infected individuals; intravenous drug users; individuals who may have been exposed to HIV-infected blood, blood products, or other HIV-contaminated body fluids; babies who are being nursed by HIV-infected mothers.

Immunostimulatory Nucleic Acid Molecules Suitable for Use in the Methods of the Invention The term "polynucleotide," as used in the context of immunostimulatory nucleic acid molecules, is a polynucleotide as defined above, and encompasses, inter alia, single- and double-stranded oligonucleotides (including deoxyribonucleotides, ribonucleotides, or both), modified oligonucleotides, and oligonucleosides, alone or as part of a larger nucleic acid construct, or as part of a conjugate with a non-nucleic acid molecule such as a polypeptides. Thus immunostimulatory nucleic acid molecules may be, for example, single-stranded DNA (ssDNA), double-stranded DNA (dsDNA), single-stranded RNA (ssRNA) or double-stranded RNA (dsRNA). Immunostimulatory nucleic acid molecules also encompasses crude, detoxified bacterial (e.g., mycobacterial) RNA or DNA, as well as enriched plasmids enriched for immunostimulatory nucleic acid molecules. In some embodiments, an "immunostimulatory nucleic acid molecules-enriched plasmid" refers to a linear or circular plasmid that comprises or is engineered to comprise a greater number of CpG motifs than normally found in mammalian DNA. Exemplary immunostimulatory nucleic acid molecules-enriched plasmids are described in, for example, Roman et al. (1997) *Nat Med.* 3(8):849–54. Modifications of oligonucleotides include, but are not limited to, modifications of the 3'OH or 5'OH group, modifications of the nucleotide base, modifications of the sugar component, and modifications of the phosphate group.

An immunostimulatory nucleic acid molecule may comprise at least one nucleoside comprising an L-sugar. The L-sugar may be deoxyribose, ribose, pentose, deoxypentose, hexose, deoxyhexose, glucose, galactose, arabinose, xylose, lyxose, or a sugar "analog" cyclopentyl group. The L-sugar may be in pyranosyl or furanosyl form.

Immunostimulatory nucleic acid molecules generally do not provide for, nor is there any requirement that they provide for, expression of any amino acid sequence encoded by the polynucleotide, and thus the sequence of a immunostimulatory nucleic acid molecule may be, and generally is, non-coding. Immunostimulatory nucleic acid molecules may comprise a linear double or single-stranded molecule, a circular molecule, or can comprise both linear and circular segments. Immunostimulatory nucleic acid molecules may be single-stranded, or may be completely or partially double-stranded.

In some embodiments, an immunostimulatory nucleic acid molecule of the invention is an oligonucleotide, e.g., consists of a sequence of from about 6 to about 200, from about 10 to about 100, from about 12 to about 50, or from about 15 to about 25, nucleotides in length.

In other embodiments, an immunostimulatory nucleic acid molecule is part of a larger nucleotide construct (e.g., a plasmid vector, a viral vector, or other such construct). A wide variety of plasmid and viral vector are known in the art, and need not be elaborated upon here. A large number of such vectors has been described in various publications, including, e.g., *Current Protocols in Molecular Biology,* (F. M. Ausubel, et al., Eds. 1987, and updates). Many vectors are commercially available.

Immunostimulatory Nucleic Acid Molecules Comprising a CpG Motif

In some embodiments, the immunostimulatory nucleic acid molecules used in the invention comprise at least one unmethylated CpG motif. In general, these immunostimulatory nucleic acid molecules increase a Th1 response in an individual. The relative position of any CpG sequence in a polynucleotide having immunostimulatory activity in certain mammalian species (e.g., rodents) is 5'-CG-3' (i.e., the C is in the 5' position with respect to the G in the 3' position). Immunostimulatory nucleic acid molecules can be conveniently obtained by substituting the cytosine in the CpG dinucleotide with another nucleotide, particularly a purine nucleotide.

Exemplary immunostimulatory nucleic acid molecules useful in the invention include, but are not necessarily limited to, those comprising the following core nucleotide sequences: 1) hexameric core sequences comprising "CpG" motifs or comprising XpY motifs, where X cannot be C if Y is G and vice-versa; 2) octameric core sequences comprising "CpG" motifs or comprising XpY motifs, where X cannot be C if Y is G and vice-versa; and 3) inosine and/or uracil substitutions for nucleotides in the foregoing hexameric or octameric sequences for use as RNA immunostimulatory nucleic acid molecule (e.g., substituting uracil for thymine and/or substituting inosine for a purine nucleotide). As used herein, "core sequence" in the context of an immunostimulatory nucleic acid molecule refers to a minimal sequence that provides for, factilitates, or confers the immunostimulatory activity of the nucleic acid molecule.

Exemplary consensus CpG motifs of immunostimulatory nucleic acid molecules useful in the invention include, but are not necessarily limited to:

5'-Purine-Purine-[C]-[G]-Pyrimidine-Pyrimidine-3', in which the immunostimulatory nucleic acid molecule comprises a CpG motif flanked by at least two purine nucleotides (e.g., GG, GA, AG, AA, II, etc.,) and at least two pyrimidine nucleotides (CC, TT, CT, TC, UU, etc.);

5'-Purine-TCG-Pyrimidine-Pyrimidine-3';

5'-[TCG]$_n$-3', where n is any integer that is 1 or greater, e.g., to provide a poly-TCG immunostimulatory nucleic acid molecule (e.g., where n=3, the polynucleotide comprises the sequence 5'-TCGTCGTCG-3'); and 5'-Purine-Purine -CG-Pyrimidine-Pyrimidine-CG-3'.

The core structure of immunostimulatory nucleic acid molecules useful in the invention may be flanked upstream and/or downstream by any number or composition of nucleotides or nucleosides. In some embodiments, the core sequence of immunostimulatory nucleic acid molecules are at least 6 bases or 8 bases in length, and the complete immunostimulatory nucleic acid molecules (core sequences plus flanking sequences 5', 3' or both) are usually between 6 bases or 8 bases, and up to about 200 bases in length to enhance uptake of the immunostimulatory nucleic acid molecules. Those of ordinary skill in the art will be familiar with, or can readily identify, reported nucleotide sequences of known immunostimulatory nucleic acid molecules for reference in preparing immunostimulatory nucleic acid molecules, see, e.g., Yamamoto, et al., (1992) *Microbiol. Immunol.*, 36:983; Ballas, et al., (1996) *J. Immunol.*, 157:1840; Klinman, et al., (1997) *J. Immunol*, 158:3635; Sato, et al., (1996) *Science*, 273:352, each of which are incorporated herein by reference. In addition, immunostimulatory nucleic acid molecules useful in the invention have been described in, for example, PCT publication nos. WO 98/16427, WO 98/55495, and WO 99/11275.

Exemplary DNA-based immunostimulatory nucleic acid molecules useful in the invention include, but are not necessarily limited to, polynucleotides comprising the following nucleotide sequences: AGCGCT, AGCGCC, AGCGTT, AGCGTC, AACGCT, AACGCC, AACGTT, AACGTC, GGCGCT, GGCGCC, GGCGTT, GGCGTC, GACGCT, GACGCC, GACGTT, GACGTC, GTCGTC, GTCGCT, GTCGTT, GTCGCC, ATCGTC, ATCGCT, ATCGTT, ATCGCC, TCGTCG, and TCGTCGTCG.

Exemplary DNA-based immunostimulatory nucleic acid molecules useful in the invention include, but are not necessarily limited to, polynucleotides comprising the following octameric nucleotide sequences: AGCGCTCG, AGCGCCCG, AGCGTTCG, AGCGTCCG, AACGCTCG, AACGCCCG, AACGTTCG, AACGTCCG, GGCGCTCG, GGCGCCCG, GGCGTTCG, GGCGTCCG, GACGCTCG, GACGCCCG, GACGTTCG, and GACGTCCG.

Immunostimulatory nucleic acid molecules useful in the invention can comprise one or more of any of the above CpG motifs. For example, immunostimulatory nucleic acid molecules useful in the invention can comprise a single instance or multiple instances (e.g., 2, 3, 5 or more) of the same CpG motif. Alternatively, the immunostimulatory nucleic acid molecules can comprises multiple CpG motifs (e.g., 2, 3, 5 or more) where at least two of the multiple CpG motifs have different consensus sequences, or where all CpG motifs in the immunostimulatory nucleic acid molecules have different consensus sequences.

Immunostimulatory nucleic acid molecules useful in the invention may or may not include palindromic regions. If present, a palindrome may extend only to a CpG motif, if present, in the core hexamer or octamer sequence, or may encompass more of the hexamer or octamer sequence as well as flanking nucleotide sequences.

Modifications

Immunostimulatory nucleic acid molecules of the invention can be modified in a variety of ways. For example, the immunostimulatory nucleic acid molecules can comprise backbone phosphate group modifications (e.g., methylphosphonate, phosphorothioate, phosphoroamidate and phosphorodithioate internucleotide linkages), which modifications can, for example, confer inherent anti-microbial activity on the immunostimulatory nucleic acid molecule and enhance their stability in vivo, making them particularly useful in therapeutic applications. A particularly useful phosphate group modification is the conversion to the phosphorothioate or phosphorodithioate forms of an immunostimulatory nucleic acid molecule. In addition to their potentially anti-microbial properties, phosphorothioates and phosphorodithioates are more resistant to degradation in vivo than their unmodified oligonucleotide counterparts, increasing the half-lives of the immunostimulatory nucleic acid molecules and making them more available to the subject being treated.

Other modified immunostimulatory nucleic acid molecules encompassed by the present invention include immunostimulatory nucleic acid molecules having modifications at the 5' end, the 3' end, or both the 5' and 3' ends. For example, the 5' and/or 3' end can be covalently or non-covalently associated with a molecule (either nucleic acid, non-nucleic acid, or both) to, for example, increase the bio-availability of the immunostimulatory nucleic acid molecules, increase the efficiency of uptake where desirable, facilitate delivery to cells of interest, and the like. Exemplary molecules for conjugation to the immunostimulatory nucleic acid molecules include, but are not necessarily limited to, cholesterol, phospholipids, fatty acids, sterols, oligosaccharides, polypeptides (e.g., immunoglobulins), peptides, antigens (e.g., peptides, small molecules, etc.), linear or circular nucleic acid molecules (e.g., a plasmid), and the like. Additional immunostimulatory nucleic acid conjugates, and methods for making same, are known in the art and described in, for example, WO 98/16427 and WO 98/55495. Thus, the term "immunostimulatory nucleic acid molecule" includes conjugates comprising an immunostimulatory nucleic acid molecule. The immunostimulatory nucleic acid molecule and the antigen may be administered substantially simultaneously, or the immunostimulatory nucleic acid molecule may be administered before or after the antigen. Generally, the immunostimulatory nucleic acid molecule and the antigen are administered within about 72 hours, about 48 hours, about 24 hours, about 12 hours, about 8 hours, about 4 hours, about 2 hours, about 1 hour, or about 30 minutes or less, of each other.

Immunostimulatory nucleic acid molecule may be administered separately from antigen, in admixture with antigen, or the immunostimulatory nucleic acid can be proximately associated with (e.g., conjugated or brought into spatial proximity by other means, as described in more detail below) one or more antigens (or the antigen can be proximately associated with one or more immunostimulatory nucleic acid molecules). Generally, and most preferably, an immunomodulatory nucleic acid and an antigen are proximately associated at a distance effective to enhance the immune response generated compared to the administration of the ISS and antigen as an admixture. For a detailed discussion of method for proximate association of a polynucleotide and an antigen see, e.g., PCT Publication WO 00/21556, incorporated herein by reference.

In one embodiment, the immunostimulatory nucleic acid molecule and the antigen are provided as conjugates. Particular conjugates which may be useful in the methods of the present invention include conjugates of an immunostimulatory nucleic acid molecule and a polypeptide associated with a tumor; and conjugates of an immunostimulatory nucleic acid molecule and a peptide associated with an pathogenic organism.

The polypeptide may be a naturally-occurring polypeptide associated with a tumor or with a pathogenic organism; or a synthetic analog of a naturally-occurring polypeptide associated with a tumor or with a pathogenic organism. A peptoid corresponding to a naturally-occurring polypeptide associated with a tumor or with a pathogenic organism. Peptoid compounds and methods for their preparation are described in WO 91/19735.

Any of a variety of known tumor-specific antigens or tumor-associated antigens (TAA) can be used in a conjugate with an immunostimulatory nucleic acid molecule. The entire TAA may be, but need not be, used. Instead, a portion of a TAA, e.g., an epitope, may be used. Tumor-associated antigens (or epitope-containing fragments thereof) which may be used into YFV include, but are not limited to, MAGE-2, MAGE-3, MUC-1, MUC-2, HER-2, high molecular weight melanoma-associated antigen MAA, GD2, carcinoembryonic antigen (CEA), TAG-72, ovarian-associated antigens OV-TL3 and MOV18, TUAN, alpha-feto protein (AFP), OFP, CA-125, CA-50, CA-19-9, renal tumor-associated antigen G250, EGP-40 (also known as EpCAM), S100 (malignant melanoma-associated antigen), p53, and p21ras. A synthetic analog of any TAA (or epitope thereof), including any of the foregoing, may be used. Furthermore, combinations of one or more TAAs (or epitopes thereof) may be included in the conjugate. For example, two or more TAA epitopes may be conjugated in tandem to an immunostimulatory nucleic acid molecule, with or without an intervening linker molecule.

Any of a variety of polypeptides associated with intracellular pathogens may be used in a conjugate with an immunostimulatory nucleic acid molecule. Polypeptides and peptide epitopes associated with intracellular pathogens are any polypeptide associated with (e.g., encoded by) an intracellular pathogen, fragments of which are displayed together with MHC Class I molecule on the surface of the infected cell such that they are recognized by, e.g., bound by a T-cell antigen receptor on the surface of, a CD8$^+$ lymphocyte. Polypeptides and peptide epitopes associated with intracellular pathogens are known in the art and include, but are not limited to, antigens associated with human immunodeficiency virus, e.g., HIV gp120, or an antigenic fragment thereof; cytomegalovirus antigens; Mycobacterium antigens (e g., *Mycobacterium avium, Mycobacterium tuberculosis,* and the like); *Pneumocystic carinii* (PCP) antigens; malarial antigens, including, but not limited to, antigens associated with *Plasmodium falciparum* or any other malarial species, such as 41-3, AMA-1, CSP, PFEMP-1, GBP-130, MSP-1, PFS-16, SERP, etc.; fungal antigens; yeast antigens (e.g., an antigen of a Candida spp.); toxoplasma antigens, including, but not limited to, antigens associated with *Toxoplasma gondii, Toxoplasma encephalitis,* or any other Toxoplasma species; Epstein-Barr virus (EBV) antigens; and the like.

A polypeptide may be conjugated directly or indirectly, e.g., via a linker molecule, to an immunostimulatory nucleic acid molecule. A wide variety of linker molecules are known in the art and can be used in the conjugates. The linkage from the peptide to the oligonucleotide may be through a peptide reactive side chain, or the N- or C-terminus of the peptide. Linkage from the oligonucleotide to the peptide may be at either the 3' or 5' terminus, or internal. A linker may be an organic, inorganic, or semi-organic molecule, and may be a polymer of an organic molecule, an inorganic molecule, or a co-polymer comprising both inorganic and organic molecules.

If present, the linker molecules are generally of sufficient length to permit oligonucleotides and/or polynucleotides and a linked polypeptide to allow some flexible movement between the oligonucleotide and the polypeptide. The linker molecules are generally about 6–50 atoms long. The linker molecules may also be, for example, aryl acetylene, ethylene glycol oligomers containing 2–10 monomer units, diamines, diacids, amino acids, or combinations thereof. Other linker molecules which can bind to oligonucleotides may be used in light of this disclosure.

Peptides may be synthesized chemically or enzymatically, may be produced recombinantly, may be isolated from a natural source, or a combination of the foregoing. Peptides may be isolated from natural sources using standard methods of protein purification known in the art, including, but not limited to, HPLC, exclusion chromatography, gel electrophoresis, affinity chromatography, or other purification technique. One may employ solid phase peptide synthesis techniques, where such techniques are known to those of skill in the art. See Jones, *The Chemical Synthesis of Peptides* (Clarendon Press, Oxford)(1994). Generally, in such methods a peptide is produced through the sequential additional of activated monomeric units to a solid phase bound growing peptide chain. Well-established recombinant DNA techniques can be employed for production of peptides.

Formulations

In general, immunostimulatory nucleic acid molecules are prepared in a pharmaceutically acceptable composition for delivery to a host. Pharmaceutically acceptable carriers preferred for use with the immunostimulatory nucleic acid molecules of the invention may include sterile aqueous of non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/ aqueous solutions, emulsions or suspensions, and microparticles, including saline and buffered media. Parenteral vehicles include sodium chloride solution, Ringer's dextrose, dextrose and sodium chloride, lactated Ringer's or fixed oils. Intravenous vehicles include fluid and nutrient replenishers, electrolyte replenishers (such as those based on Ringer's dextrose), and the like. A composition comprising a immunostimulatory nucleic acid molecule may also be lyophilized using means well known in the art, for subsequent reconstitution and use according to the invention.

In general, the pharmaceutical compositions can be prepared in various forms, such as granules, tablets, pills, suppositories, capsules, suspensions, salves, lotions and the like. Pharmaceutical grade organic or inorganic carriers and/or diluents suitable for oral and topical use can be used to make up compositions comprising the therapeutically-active compounds. Diluents known to the art include aqueous media, vegetable and animal oils and fats. Stabilizing agents, wetting and emulsifying agents, salts for varying the osmotic pressure or buffers for securing an adequate pH value, and skin penetration enhancers can be used as auxiliary agents. Preservatives and other additives may also be present such as, for example, antimicrobials, antioxidants, chelating agents, and inert gases and the like. In one embodiment, as discussed above, the immunostimulatory nucleic acid molecule formulation comprises an additional anti-mycobacterial agent.

Immunostimulatory nucleic acid molecules can be administered in the absence of agents or compounds that might facilitate uptake by target cells (e.g., as a "naked" polynucleotide, e.g., a polynucleotide that is not encapsulated by a viral particle, a liposome, or any other macromolecule). Immunostimulatory nucleic acid molecules can be administered with compounds that facilitate uptake of immunostimulatory nucleic acid molecules by target cells (e.g., by macrophages) or otherwise enhance transport of an immunostimulatory nucleic acid molecule to a treatment site for action. Absorption promoters, detergents and chemical irritants (e.g., keratinolytic agents) can enhance transmission of an immunostimulatory nucleic acid molecule composition into a target tissue (e.g., through the skin). For general principles regarding absorption promoters and detergents which have been used with success in mucosal delivery of organic and peptide-based drugs, see, e.g., Chien, *Novel Drug Delivery Systems,* Ch. 4 (Marcel Dekker, 1992). Examples of suitable nasal absorption promoters in particular are set forth at Chien, supra at Ch. 5, Tables 2 and 3; milder agents are preferred. Suitable agents for use in the method of this invention for mucosal/nasal delivery are also described in Chang, et al., *Nasal Drug Delivery,* "Treatise on Controlled Drug Delivery", Ch. 9 and Tables 3–4B thereof, (Marcel Dekker, 1992). Suitable agents which are known to enhance absorption of drugs through skin are described in Sloan, Use of Solubility Parameters from Regular Solution Theory to Describe Partitioning-Driven Processes, Ch. 5, "Prodrugs: Topical and Ocular Drug Delivery" (Marcel Dekker, 1992), and at places elsewhere in the text. All of these references are incorporated herein for the sole purpose of illustrating the level of knowledge and skill in the art concerning drug delivery techniques.

A colloidal dispersion system may be used for targeted delivery of the immunostimulatory nucleic acid molecules to specific tissue. Colloidal dispersion systems include macromolecule complexes, nanocapsules, microspheres, beads, and lipid-based systems including oil-in-water emulsions, micelles, mixed micelles, and liposomes.

Liposomes are artificial membrane vesicles which are useful as delivery vehicles in vitro and in vivo. It has been shown that large unilamellar vesicles (LUV), which range in size from 0.2–4.0 Fm can encapsulate a substantial percentage of an aqueous buffer comprising large macromolecules. RNA and DNA can be encapsulated within the aqueous interior and be delivered to cells in a biologically active form (Fraley, et al., (1981) *Trends Biochem. Sci.,* 6:77). The composition of the liposome is usually a combination of phospholipids, particularly high-phase-transition-temperature phospholipids, usually in combination with steroids, especially cholesterol. Other phospholipids or other lipids may also be used. The physical characteristics of liposomes depend on pH, ionic strength, and the presence of divalent cations. Examples of lipids useful in liposome production include phosphatidyl compounds, such as phosphatidylglycerol, phosphatidylcholine, phosphatidylserine, phosphatidylethanolamine, sphingolipids, cerebrosides, and gangliosides. Particularly useful are diacylphosphatidylglycerols, where the lipid moiety contains from 14–18 carbon atoms, particularly from 16–18 carbon atoms, and is saturated. Illustrative phospholipids include egg phosphatidylcholine, dipalmitoylphosphatidylcholine and distearoylphosphatidylcholine.

Where desired, targeting of liposomes can be classified based on anatomical and mechanistic factors. Anatomical classification is based on the level of selectivity, for example, organ-specific, cell-specific, and organelle-specific. Mechanistic targeting can be distinguished based upon whether it is passive or active. Passive targeting utilizes the natural tendency of liposomes to distribute to cells of the reticulo-endothelial system (RES) in organs which contain sinusoidal capillaries. Active targeting, on the other hand, involves alteration of the liposome by coupling the liposome to a specific ligand such as a monoclonal antibody, sugar, glycolipid, or protein, or by changing the composition or size of the liposome in order to achieve targeting to organs and cell types other than the naturally occurring sites of localization.

The surface of the targeted delivery system may be modified in a variety of ways. In the case of a liposomal targeted delivery system, lipid groups can be incorporated into the lipid bilayer of the liposome in order to maintain the targeting ligand in stable association with the liposomal bilayer. Various well known linking groups can be used for joining the lipid chains to the targeting ligand (see, e.g., Yanagawa, et al., (1988) *Nuc. Acids Symp. Ser.,* 19:189; Grabarek, et al., (1990) *Anal. Biochem.,* 185:131; Staros, et al., (1986) *Anal. Biochem.* 156:220 and Boujrad, et al., (1993) *Proc. Natl. Acad. Sci. USA,* 90:5728). Targeted delivery of immunostimulatory nucleic acid molecules can also be achieved by conjugation of the immunostimulatory nucleic acid molecules to a the surface of viral and non-viral recombinant expression vectors, to an antigen or other ligand, to a monoclonal antibody or to any molecule which has the desired binding specificity.

An immunostimulatory nucleic acid molecule can be administered to an individual in combination (e.g., in the same formulation or in separate formulations) with another therapeutic agent ("combination therapy"). The immunostimulatory nucleic acid molecule can be administered in admixture with another therapeutic agent or can be administered in a separate formulation. When administered in separate formulations, an immunostimulatory nucleic acid molecule and another therapeutic agent can be administered substantially simultaneously (e.g., within about 60 minutes, about 50 minutes, about 40 minutes, about 30 minutes, about 20 minutes, about 10 minutes, about 5 minutes, or about 1 minute of each other) or separated in time by about 1 hour, about 2 hours, about 4 hours, about 6 hours, about 10 hours, about 12 hours, about 24 hours, about 36 hours, or about 72 hours, or more.

Therapeutic agents that can be administered in combination therapy, such as anti-inflammatory, anti-viral, anti-fungal, anti-mycobacterial, antibiotic, amoebicidal, trichomonocidal, analgesic, anti-neoplastic, anti-hypertensives, anti-microbial and/or steroid drugs, to treat antiviral infections. In some embodiments, patients with a viral or bacterial infection are treated with a combination of one or more immunostimulatory nucleic acid molecules with one or more of the following; beta-lactam antibiotics, tetracyclines, chloramphenicol, neomycin, gramicidin, bacitracin, sulfonamides, nitrofurazone, nalidixic acid, cortisone, hydrocortisone, betamethasone, dexamethasone, fluocortolone, prednisolone, triamcinolone, indomethacin, sulindac, acyclovir, amantadine, rimantadine, recombinant soluble CD4 (rsCD4), anti-receptor antibodies (e.g., for rhinoviruses), nevirapine, cidofovir (Vistide™), trisodium phosphonoformate (Foscarnet™), famcyclovir, pencyclovir, valacyclovir, nucleic acid/replication inhibitors, interferon, zidovudine (AZT, Retrovir™), didanosine (dideoxyinosine, ddI, Videx™), stavudine (d4T, Zerit™), zalcitabine (dideoxycytosine, ddC, Hivid™), nevirapine (Viramune™), lamivudine (Epivir™, 3TC), protease inhibitors, saquinavir (Invirase™, Fortovase™), ritonavir (Norvir™), nelfinavir (Viracept™), efavirenz (Sustiva™), abacavir (Ziagen™), amprenavir (Agenerase™) indinavir (Crixivan™), ganciclovir, AzDU, delavirdine (Rescriptor™), kaletra, trizivir, rifampin, clathiromycin, erythropoietin, colony stimulating factors (G-CSF and GM-CSF), non-nucleoside reverse transcriptase inhibitors, nucleoside inhibitors, adriamycin, fluorouracil, methotrexate, asparaginase and combinations thereof.

Routes of Administration

Immunostimulatory nucleic acid molecules are administered to an individual using any available method and route suitable for drug delivery, including in vivo and ex vivo methods, as well as systemic, mucosal, and localized routes of administration.

Conventional and pharmaceutically acceptable routes of administration include intranasal, intramuscular, intratracheal, intratumoral, subcutaneous, intradermal, topical application, intravenous, rectal, nasal, oral and other parenteral routes of administration. Routes of administration may be combined, if desired, or adjusted depending upon the immunostimulatory nucleic acid and/or the desired effect on the immune response. The immunostimulatory nucleic acid composition can be administered in a single dose or in multiple doses, and may encompass administration of booster doses, to elicit and/or maintain the desired effect on the immune response.

Immunostimulatory nucleic acid molecules can be administered to a host using any available conventional methods and routes suitable for delivery of conventional drugs, including systemic or localized routes. In general, routes of administration contemplated by the invention include, but are not necessarily limited to, enteral, parenteral, or inhalational routes. Inhalational routes may be preferred in cases of pulmonary involvement, particularly in view of the activity of certain immunostimulatory nucleic acid molecules as a mucosal adjuvant.

Inhalational routes of administration (e.g., intranasal, intrapulmonary, and the like) are particularly useful in stimulating an immune response for prevention or treatment of infections of the respiratory tract. Such means include inhalation of aerosol suspensions or insufflation of the polynucleotide compositions of the invention. Nebulizer devices, metered dose inhalers, and the like suitable for delivery of polynucleotide compositions to the nasal mucosa, trachea and bronchioli are well-known in the art and will therefore not be described in detail here. For general review in regard to intranasal drug delivery, see, e.g., Chien, *Novel Drug Delivery Systems,* Ch. 5 (Marcel Dekker, 1992).

Parenteral routes of administration other than inhalation administration include, but are not necessarily limited to, topical, transdermal, subcutaneous, intramuscular, intraorbital, intraspinal, intrasternal, and intravenous routes, i.e., any route of administration other than through the alimentary canal. Parenteral administration can be carried to effect systemic or local delivery of immunostimulatory nucleic acid molecules.

Systemic administration typically involves intravenous, intradermal, subcutaneous, or intramuscular administration or systemically absorbed topical or mucosal administration of pharmaceutical preparations. Mucosal administration includes administration to the respiratory tissue, e.g., by inhalation, nasal drops, ocular drop, etc.; anal or vaginal routes of administration, e.g., by suppositories; and the like.

Immunostimulatory nucleic acid molecules can also be delivered to the subject by enteral administration. Enteral routes of administration include, but are not necessarily limited to, oral and rectal (e.g., using a suppository) delivery.

Methods of administration of immunostimulatory nucleic acid molecules through the skin or mucosa include, but are not necessarily limited to, topical application of a suitable pharmaceutical preparation, transdermal transmission, injection and epidermal administration. For transdermal transmission, absorption promoters or iontophoresis are suitable methods. For review regarding such methods, those of ordinary skill in the art may wish to consult Chien, supra at Ch. 7. Iontophoretic transmission may be accomplished using commercially available "patches" which deliver their product continuously via electric pulses through unbroken skin for periods of several days or more. An exemplary patch product for use in this method is the LECTRO PATCH™ (manufactured by General Medical Company, Los Angeles, Calif.) which electronically maintains reservoir electrodes at neutral pH and can be adapted to provide dosages of differing concentrations, to dose continuously and/or to dose periodically.

Epidermal administration can be accomplished by mechanically or chemically irritating the outermost layer of the epidermis sufficiently to provoke an immune response to the irritant. An exemplary device for use in epidermal administration employs a multiplicity of very narrow diameter, short tynes which can be used to scratch immunostimulatory nucleic acid molecules coated onto the tynes into the skin. The device included in the MONO-VACC™ tuberculin test (manufactured by Pasteur Merieux, Lyon, France) is suitable for use in epidermal administration of immunostimulatory nucleic acid molecules.

The invention also contemplates opthalmic administration of immunostimulatory nucleic acid molecules, which generally involves invasive or topical application of a pharmaceutical preparation to the eye. Eye drops, topical cremes and injectable liquids are all examples of suitable formulations for delivering drugs to the eye.

Dosages

Although the dosage used will vary depending on the clinical goals to be achieved, a suitable dosage range is one which provides up to about 1 μg to about 1,000 μg or about 10,000 μg of immunostimulatory nucleic acid molecule can be administered in a single dosage. Alternatively, a target dosage of immunostimulatory nucleic acid molecule can be considered to be about 1–10 μM in a sample of host blood drawn within the first 24–48 hours after administration of immunostimulatory nucleic acid molecules. Based on current studies, immunostimulatory nucleic acid molecules are believed to have little or no toxicity at these dosage levels.

It should be noted that the immunotherapeutic activity of immunostimulatory nucleic acid molecules is generally dose-dependent. Therefore, to increase immunostimulatory nucleic acid molecules potency by a magnitude of two, each single dose is doubled in concentration. Increased dosages may be needed to achieve the desired therapeutic goal. The invention thus contemplates administration of "booster" doses to provide and maintain a desired immune response. For example, immunostimulatory nucleic acid molecules may be administered at intervals ranging from at least every two weeks to every four weeks (e.g., monthly intervals) (e.g., every four weeks).

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric.

Example 1

Conjugates of OVA and an Immunostimulatory Nucleic Acid Molecule Induce High Antigen-specific CTL Activity Methods Protein immunostimulatory sequence oligonucleotide (ISS-ODN) (PIC) conjugate synthesis All chemicals were purchased from Sigma (St. Louis, Mo.) unless otherwise noted. Ovalbumin (chicken egg albumin, Grade VI) was activated with 20-fold molar excess of sulfosuccinimidyl-4-(N-maleimidomethyl) cyclohexane-1-carboxylate(sulfo-SMCC, Pierce, Rockford, Ill.) at room temperature for one hour. This modified the amino side chains of L-lysine residues by the addition of maleimide groups. Residual reagents were removed by chromatography on a G-25 desalting column (Amersham Pharmacia Biotech, Piscataway, N.J.). 5'-disulfide-ISS-ODN were reduced with 200 mM TRIS (2-carboxyethyl) phosphine (TCEP, Pierce) at room temperature for one hour, and residual reagents were removed by chromatography on a G-25 desalting column. The resulting 5'-thio-ISS-ODN were mixed with the modified OVA at a 5:1 molar ratio (ISS-ODN:OVA) and incubated overnight at room temperature. 5' Disulfide-linked phosphorothioate ISS-ODN, sequence 5'-disulfide-TGACTGTGAACGTTCGAGATGA-3' (SEQ ID NO:1) and mutated ODN, sequence 5'-disulfide-TGACTGTG AACCTTCGAGATGA-3' (SEQ ID NO:2) were purchased from Tri-Link Biotechnology (San Diego, Calif.). Non-reducing SDS-PAGE was performed using Novex (San Diego, Calif.) 10–20% Tricine mini-gels run at a constant voltage of 100 V. Protein concentration was determined by Bradford assay (Bio-Rad, Hercules, Calif.). PIC samples were determined to be LPS-free by Limulus amebocyte lysate assay (BioWhittaker, Walkersville, Md.).

Vaccines

Single stranded phosphorothioate ISS-ODN, sequence 5'-TGACTGTGAACGTTCGAGATGA-3' (SEQ ID NO:3) were purchased from Tri-Link Biotechnology. Plasmid pACB-OVA was as described. Corr et al. (1997) *J. Immunol.* 159:4999–5004; and Raz et al. (1996) *Proc. Natl. Acad. Sci. USA* 93:5141–5145.

Peptides

H-$2^b$ MHC class I-restricted peptides were purchased from Peptido Genics Research (Fullerton, Calif.). OVA peptide: $NH_2$-SIINFEKL-COOH (SEQ ID NO:4). Influenza virus nucleoprotein (NP) peptide (negative control): $NH_2$-ASNENMETM-COOH (SEQ ID NO:5).

CTL Assay

The CTL assay was conducted as follows. Briefly, $2 \times 10^6$ effector splenocytes were restimulated in culture for five days with $1.8 \times 10^7$ OVA peptide-pulsed stimulator splenocytes and 50 U/ml recombinant human IL-2 (PharMingen) in RPMI culture medium (Irvine Scientific, Santa Ana, Calif.) supplemented with 10% heatBinactivated fetal calf serum (FCS), 50 mM β-mercaptoethanol (Sigma), 2 mM L-glutamine, 100 U/ml penicillin, and 100 μg/ml streptomycin (RP 10). After restimulation, viable lymphocytes were recovered by centrifugation over Ficoll lympholyte M (Cedarlane Laboratories, Ltd., Ontario, Canada) at room temperature for 20 minutes. Cells were washed once in RP2 (RPMI+2% FCS) and then serially-diluted to several effector to target cell ratios (E:T) in 96-well U-bottom culture plates (Costar, Cambridge, Mass.) in colorless RPMI (Irvine Scientific) supplemented with 2% bovine serum albumin (Sigma), 2 mM L-glutamine, 100 U/ml penicillin, and 100 μg/ml streptomycin. Target EL4 cells were pulsed with OVA or NP peptide at 37° C. for one hour, then washed three times with colorless RPMI. Plates were incubated for 4 hours, and supernatants recovered. Specific lysis was assayed with the CytoTox 96 kit (Promega, Madison, Wis.) according to the manufacturer's instructions.

Results

Synthesis of OVA-ISS Conjugates

Hen egg ovalbumin (OVA) was used as a model antigen in the series of experiments described herein. The OVA-ISS-conjugates were prepared as described above. PIC was qualitatively evaluated by non-reducing sodium dodecyl sulfate-polyacrylamide gel electrophoresis (SDS-PAGE). Bands corresponding to PIC were visualized by short-wave UV shadowing on a silica gel thin layer chromatography plate, followed by Coomassie G-250 staining to detect protein bands. A ladder is visible corresponding to increasing ISS-ODN:OVA ratios in the conjugate. PIC at ISS-ODN:OVA ratios higher than 1:1 stain poorly with Coomassie blue due to the high concentration of acidic ODN. The average molar ratio of ISS-ODN:OVA in this series of experiments was ~2.4:1. Conjugate was also synthesized with mutated ODN that do not contain CpG dinucleotides, and this mutated PIC (designated "mPIC") was used as a control.

PIC Vaccination Induces High Antigen-specific CTL Activity

To determine if PIC is more efficient than co-administration of OVA and ISS-ODN or plasmid DNA vaccine, wild type (wt) C57B1/6 mice were immunized with PIC and the resultant CTL activity was evaluated. For comparison, test groups were immunized with mPIC, OVA+ISS-ODN co-administration, pACB-OVA (a plasmid DNA vaccine that contains ISS motifs), and OVA alone. An untreated group was also included. In secondary CTL assays, PIC vaccination resulted in remarkably high activity, with 91±5% specific lysis observed at a 25:1 effector to target (E:T) ratio and 92±4% at a 1:1 ratio, indicating that activity was at a plateau even at a high dilution.

These results are shown in FIG. 1. Test animals were immunized intradermally (i.d.) at the tail base on days zero and 14 with the following vaccines: PIC (50 µg, closed square), OVA+ISS-ODN co-administration (50 µgg each, closed diamond), mPIC (50 µg, open diamond), pACB-OVA (50 µg, closed circle), or OVA alone (50 µg, closed triangle). Vaccines were diluted in sterile normal saline solution. At six weeks, total splenocytes were isolated and restimulated in culture for five days. Secondary CTL activity was determined by LDH release. Targets were EL-4 cells loaded with either MHC class I-restricted OVA peptide or influenza virus nucleoprotein peptide (target control, open square). Error bars indicate the standard error of the mean. Data are averaged from four to five mice per group, and are representative of four experiments.

At a 0.2:1 E:T ratio, specific lysis was 64±10%. This activity was significantly higher than that observed in OVA+ISS co-administration, despite the higher molar ratio of ISS-ODN:OVA protein in the latter treatment (6:1 in the co-administration vs. ~2.4:1 in the PIC).

PIC also elicited higher levels of CTL activity than pACB-OVA vaccination. Animals immunized with mPIC exhibited low CTL activity (33±2% specific lysis at 25:1 ratio), which is comparable to the non-specific adjuvant activity of mutated oligonucleotide. OVA administration alone did not stimulate CTL activity. Target cells loaded with an irrelevant MHC class I-restricted peptide were not lysed by splenocytes from OVA PIC-immunized mice, indicating that the observed response was antigen-specific. These results show that vaccination with PIC resulted in higher antigen-specific CTL activity than other ISS-based vaccines.

Example 2

Conjugates of OVA and an Immunostimulatory Nucleic Acid Molecule Induces a Th1-like Response Methods
Cytokine ELISA Purified rat anti-mouse IFNγ capture antibody and purified, biotinylated rat anti-mouse IFN$_\gamma$ detecting antibody were purchased from PharMingen (San Diego, Calif.). IL-4 capture and detecting antibodies (Duoset) were purchased from Genzyme (Cambridge, Mass.). Briefly, splenocytes were isolated as described in the previous section, and 5×10$^5$ splenocytes were aliquoted in triplicate into 96 well culture plates (Costar) in a total volume of 200 µl RP10 with and without 50 µg/ml ovalbumin (Sigma). Cultures were incubated at 37° C. with 5% CO$_2$ for three days, and then aliquots of tissue culture supernatant were removed for cytokine ELISA. Half-area 96 well plates (Costar) were coated with capture antibody diluted 1:1000 in carbonate buffer (15 mM Na$_2$CO$_3$, 35 mM NaHCO$_3$, pH 9.6), overnight at 4° C. Plates were washed with 1×BBS (160 mM NaCl, 40 mM NaOH, 200 mM Boric acid, pH 8.0) and then blocked for two hours at 37° C. with blocking buffer (1% BSA in BBS). Plates were washed and incubated with tissue culture supernates diluted 1:2 in blocking buffer overnight at 4° C. Plates were washed and incubated with detecting antibody diluted 1:1000 in blocking buffer at room temperature for one hour. Plates were washed and incubated with streptavidin-HRP conjugate (Zymed, South San Francisco, Calif.) diluted 1:2000 in blocking buffer at room temperature for one hour. Plates were washed and incubated with TMB substrate (Moss, Incorporated, Hanover, Md.). The reaction was stopped with 1M phosphoric acid (Sigma) and the plates were read at 450 nm on a Molecular Devices ThermoMax microplate reader (Sunnyvale, Calif.).

Ig ELISA

Alkaline phosphatase-conjugated goat anti-mouse IgG$_1$ and IgG$_{2a}$ were purchased from Southern Biotechnology Associates (Birmingham, Ala.). Plates were coated with serum serially diluted in blocking buffer overnight at 4° C. Plates were washed and incubated with detecting antibody diluted 1:2000 in blocking buffer. Plates were washed and incubated with 4-nitrophenyl phosphate substrate (Roche Diagnostics, Basel, Switzerland). Plates were read at 405 nm as described above.

Results

PIC Vaccination Induces a T$_h$1-like Immune Response

Figures 2A, 2B, 2C:
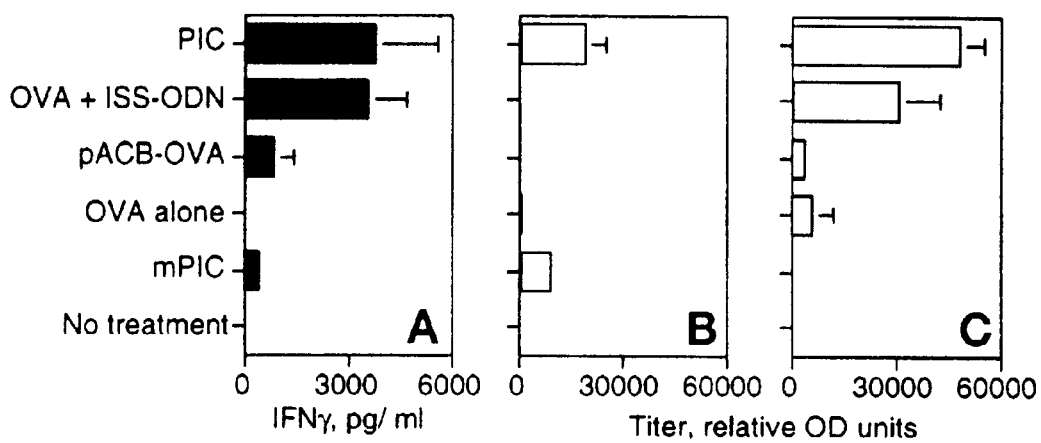
FIGS. 2A–C are graphs depicting the effects of vaccination with protein-ISS conjugates on the Th1 immune response. Total splenocytes were restimulated as described in Example 2, and IFNγ levels (FIG. 2A) were measured. IgG1 titers (FIG. 2B), and IgG2a titers (FIG. 2C) were measured in serum.

Total splenocyte cytokine production and antigen-specific isotype switching to IgG$_{2a}$ were examined to assess the T helper response to PIC vaccination. Splenocytes from the groups described in the previous section were re-stimulated in culture, and tissue culture supernatants were collected at day 3 for cytokine ELISA. PIC and OVA+ISS-ODN co-administration induced comparable levels (3800±1800 and 3600±1100 pg/ml, respectively) of IFNγ, a Th1-associated cytokine, in response to OVA stimulation. The results are shown in FIG. 2A. By comparison, pACB-OVA and mPIC vaccination resulted in IFN$_\gamma$ production approximately 20% and 10% of this amount, respectively. IL-4, a Th2-associated cytokine, was not detected in any of the groups.

IFNγ is a switch factor for IgG2a, and isotype switching to IgG2a is also a marker for Th1-biased immune responses. Serum was collected at week 6 and assayed for OVA-specific IgG$_1$ and IgG$_{2a}$ by immunoglobulin ELISA. The results are shown in FIGS. 3B and 3C. PIC induced a substantial isotype switch to IgG$_{2a}$, similar to co-administration of OVA+ISS-ODN. PIC vaccination also produced a higher titer of IgG$_1$+IgG$_{2a}$, suggesting that the magnitude of the T$_h$ and concomitant B cell response was higher. Immunization with mPIC resulted in antigen-specific IgG$_1$ production without isotype switching to IgG$_{2a}$. These data indicate that PIC vaccination promoted a T$_h$1-like helper phenotype as measured by IFN$_\gamma$ production and IgG$_{2a}$ isotype switching.

Total splenocytes were isolated as described in Example 1. Splenocytes were restimulated as described above, and IFNγ concentration in day three supernatants was determined by cytokine ELISA. Values for IFNγ concentration are shown in FIG. 2A. IgG$_1$ and IgG$_{2a}$ titers in week six serum from immunized mice are shown in FIGS. 2B and 2C, respectively. Relative titer was determined by isotype-specific ELISA. Error bars indicate the standard error of the mean. Data are averaged from four to five mice per group, and are representative of four experiments.

Example 3

Induction of CTL Activity by a Conjugate of OVA and an Immunostimulatory Nucleic Acid Molecule is Independent of MHC Class II-restricted T Cell Help Results Induction of CTL Activity by PIC is Independent of MHC Class II-restricted Help To test the hypothesis that CTL induction and $T_h1$-bias are independent in PIC vaccination, $CD4^{-/-}$ and MHC class $II^{-/-}$ gene-deficient mice were vaccinated according to the protocol described in Example 1. MHC class $II^{-/-}$ mice were included to assess the contribution of MHC class II-restricted T cell help by $CD4^-/CD8^-$ lymphocytes. The CTL responses of wt mice to PIC, OVA and ISS-ODN co-administration, and OVA alone are shown in FIG. 3A. Vaccination with either PIC or OVA+ISS-ODN elicited high antigen-specific CTL activity (61±3% and 54±2% specific lysis at a 25:1 E:T ratio, respectively) from $CD4^{-/-}$ mice, as shown in FIG. 3B. These vaccines also stimulated CTL activity (83±3% and 65±4% specific lysis, respectively) from MHC class $II^{-/-}$ mice, as shown in FIG. 3C. OVA alone did not elicit CTL activity in these groups. Plasmid pACB-OVA did not stimulate antigen-specific CTL activity in $CD4^{-/-}$ mice. Neither $CD4^{-/-}$ nor MHC class $II^{-/-}$ mice generated a $T_h1$-biased immune response to PIC vaccination as measured by $IFN_\gamma$ and $IgG_{2a}$ production. Therefore, activation of CTL activity by ISS adjuvant was independent of MHC class II-restricted T cell help. Interestingly, effector function from $CD4^{-/-}$ and MHC class $II^{-/-}$ mice immunized with OVA+ISS-ODN was more rapidly diluted at 5:1 and 1:1 E:T ratios compared to PIC vaccination, suggesting that co-administration was less efficient than PIC under conditions where T cell help was not available.

FIGS. 3A–C show the results of the above-described experiments performed in wild type (FIG. 3A), $CD4^{-/-}$ (FIG. 3B), and MHC class $II^{-/-}$ (FIG. 3C) gene-deficient animals. Animals were vaccinated i.d. at the tail base on days zero and 14 with either PIC (50 µg, square), OVA+ISS-ODN (50 µg each, diamond), or OVA alone (50 µg, circle). CTL activity was determined as described in Example 1. Error bars indicate the standard error of the mean. Data are averaged from four mice per group, and are representative of two experiments.

Example 4

Vaccination with a Conjugate of OVA and an Immunostimulatory Nucleic Acid Molecule Results in Protective Immunity in Both Preventive and Therapeutic Models of Cancer Results Vaccination with PIC Results in Protective Immunity in Mouse Models of Cancer To assess the in vivo effectiveness of PIC vaccination, two mouse models of cancer were examined. In a preventive model of tumor vaccination, C57B1/6 mice were vaccinated with PIC and other ISS-based vaccines, as well as controls. The test animals were vaccinated twice, then received a lethal tumor challenge of E.G7-OVA or EL-4 cells, and tumor growth was followed for six weeks. Porgador et al. (1996). *J. Immunol.* 156:2918–2926.

Vaccination with PIC suppressed tumor growth, as shown in FIG. 4A. Vaccination with pACB-OVA also inhibited tumor growth, but to a lesser degree. OVA+ISS-ODN initially appeared to slow growth of tumor, but at later time points, this effect was reduced. Neither ISS-ODN nor OVA protein alone appeared to significantly retard tumor growth. Similarly, vaccination with mPIC, which does not contain CpG dinucleotides, did not confer protection. Immunization with ISS-based vaccines did not prevent the growth of EL-4 cells, the parental line that does not express OVA, indicating that the protective effect was antigen-specific. Treatment with ISS-based vaccines also did not appear to affect overall survival, in that there was no evidence of increased, non-tumor-related morbidity or mortality among groups that demonstrated tumor immunity over the susceptible groups.

PIC appeared to be the most effective vaccine for stimulating resistance to tumor growth in the preventive model, so it was also tested in a therapeutic model of cancer. Test animals received tumor challenge on day zero, and were subsequently immunized either on days zero, 6, and 11 (early), or on days 6, 11, and 15 (late). Early vaccination with PIC resulted in profound suppression of tumor growth relative to controls, as shown in FIG. 4B. Late vaccination with PIC induced tumor regression by 14 days, with subsequent suppression of tumor growth. These results showed that vaccination with PIC resulted in protective immunity against tumor expressing OVA in both preventive and therapeutic models of cancer.

Preventive model (FIG. 4A). Test animals were vaccinated i.d. at the tail base on days zero and 14 with the following vaccines: PIC (50 µg, closed square), mPIC (50 µg, open square), OVA+ISS-ODN co-administration (50 µg each, closed diamond), pACB-OVA (50 µg, closed triangle), or OVA alone (50 µg, closed circle). On day 28, each group received a lethal challenge of $20 \times 10^6$ E.G7-OVA cells sub-cutaneously (s.c.) in the right flank, and tumor growth was followed over the subsequent six weeks. The observed difference in tumor growth is statistically significant between the PIC and mPIC groups (two-tailed t test, p=0.05), PIC and OVA alone (p<0.02), and PIC and no treatment (p<0.025).

Therapeutic model (FIG. 4B). Test animals received s.c. tumor challenge on day zero and early (days zero, 6, and 11, open square) or late (days 6, 11, and 15, closed square) i.d. vaccination with PIC (50 µg). The observed difference in tumor growth between the PIC treatment groups and untreated controls is statistically significant (p<0.005).

PIC-induced Anti-tumor Immunity is Dependent on $CD8^+$ CTL and Independent of $CD4^+$ Cell Help PIC efficiently promotes CTL activity and $T_h1$-biased immune responses. To assess the roles of $CD8^+$ CTL activity and $CD4^+$ $T_h$-dependent mechanisms in anti-tumor immunity, $CD4^{-/-}$ and $CD8^{-/-}$ gene-deficient mice received subcutaneous tumor challenge on day zero and were immunized with PIC on days zero, 3, and 7. $CD4^{-/-}$ and wt control animals exhibited similar suppression of tumor growth, whereas $CD8^{-/-}$ mice did not suppress tumor growth, as shown in FIG. 4C. As expected, $CD4^{-/-}$ animals did not exhibit a $T_h1$-biased immune response, while $CD8^{-/-}$ mice had a response similar to wt animals. These results showed that protective anti-tumor immunity induced by PIC is mediated by $CD8^+$ CTL activity, rather than $T_h$-dependent mechanisms.

Therapeutic model in $CD4^{-/-}$ (closed square) and $CD8^{-/-}$ (open square) gene-deficient mice (FIG. 4C). Gene-deficient animals received s.c. tumor challenge on day zero and were immunized i.d. with PIC (50 µg) on days zero, 3, and 7. The observed difference in tumor growth between $CD4^{-/-}$ and $CD8^{-/-}$ groups is statistically significant (p<0.005). Tumor growth in all three plots is expressed as tumor index=square root (length×width). Data are averaged from six mice per group and are representative of two experiments each.

Example 5

Characterization of the Requirements for ISS-mediated Activation of CTL

Protocols

Mice were vaccinated with ISS+OVA as described in Example 1. CTL assays were conducted, as described in Example 1.

Bone marrow chimeras were created using a standard protocol. Briefly, femurs were harvested from TAP-/- and C57BL/6 wt donors. Bone marrow was flushed out, and a single-cell suspension in cell culture medium was made. After allowing debris to settle, the top layer of the suspension was transferred to a fresh tube. Cells were subsequently treated with anti-Thy1, anti-CD4, and anti-CD8 antibodies plus complement. The final cell culture was pelleted, the re-suspended in cell culture medium at about $10^8$ cells/ml.

Results

ISS-based Vaccines Require TAP Activity for Priming of CTL

Transporters associated with Antigen Processing (TAP) are heterodimeric proteins associated with the endoplasmic reticulum membrane, and are required for antigen presentation by MHC Class I molecules.

Figure 5:
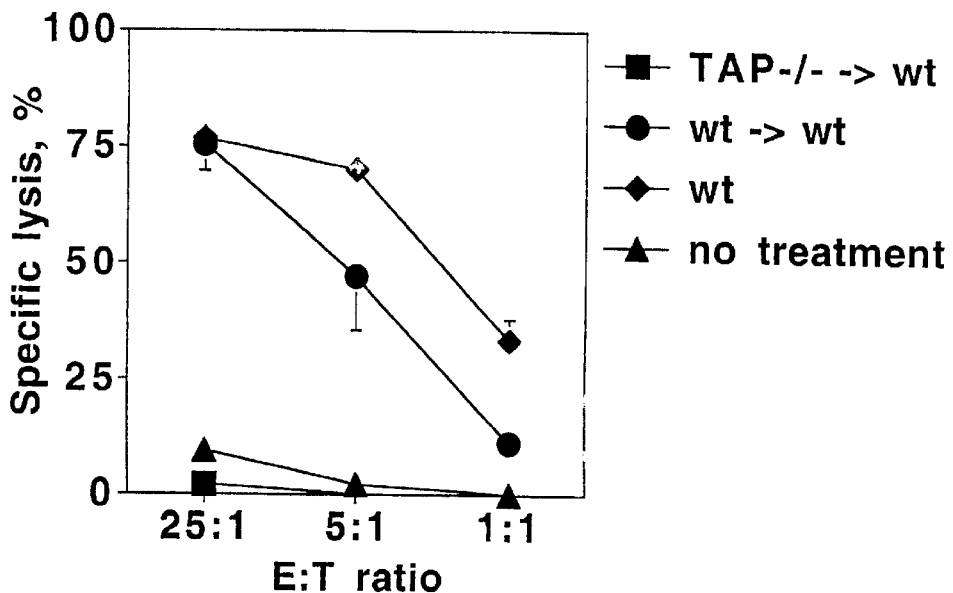
FIG. 5 is a graph depicting specific lysis versus effector:target ratio for CTL from chimeric mice made from wild-type mice and TAP$^{-/-}$ bone-marrow injected with ISS+OVA (TAP$^{-/31}$ →wt); wild-type mice with wild-type bone marrow injected with ISS+OVA (wt→wt); wild-type mice injected with ISS+OVA (wt); and wild-type mice not injected with ISS+OVA (no treatment).

Bone marrow from $TAP^{-/-}$ mice were introduced into wild type mice to create chimeras. The TAP→wt bone marrow chimeras were vaccinated, and CTL assays were conducted. As shown in FIG. 5, TAP→wt chimeras failed to generate antigen-specific CTL, whereas wt→wt chimeras did generate antigen-specific CTL, demonstrating that TAP is required for cross-presentation promoted by ISS+OVA immunization.

CD40 Signaling is not Essential for ISS-mediated CTL Activation

CD40 is a molecule found on the surface of activated macrophages and B cells, and interacts with CD40 ligand, which is expressed on the surface of effector T cells. Current models of cross-priming to soluble protein antigens suggest that APC require an initial "licensing" interaction with Th cells before they can prime naive CTL, and this interaction requires CD40 signaling.

Figure 6:
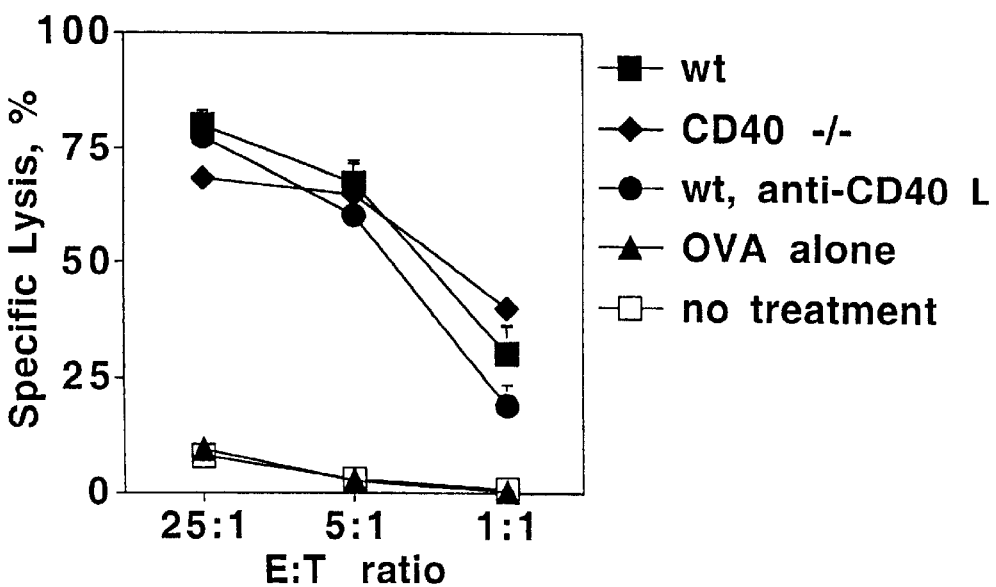
FIG. 6 is a graph depicting specific lysis versus effector:target ratio for CTL from wild-type injected with ISS+OVA (wt); CD40$^{-/-}$ mice injected with ISS+OVA; wild-type mice pre-treated with anti-CD40 ligand and injected with ISS+OVA (wt, anti-CD40 L); wild-type mice injected with OVA alone (OVA); and wild-type mice not injected with ISS+OVA (no treatment).

$CD40^{-/-}$ mice, CD40 ligand$^{-/-}$ mice, and wild-type mice pre-treated with anti-CD40 ligand antibody were vaccinated as described in Example 1. As shown in FIG. 6, wt mice immunized with ISS+OVA demonstrated antigen-specific CTL activity of 80±2% specific lysis at a 25:1 effector:target (E:T) ratio. Lytic activity from splenocytes of CD40-/- mice (68±2% at 25:1 E:T) and wt mice pre-treated with anti-CD40L monoclonal antibody (mAb) (78±7% at 25:1 E:T ratio) did not differ significantly from that of untreated wt mice. Thus, in contrast to current models for cross-priming to soluble protein antigens, CD40 signaling is not essential for direct activation of CTL by ISS-based vaccines.

Activation of CTL by ISS Vaccine Requires B7-CD28 Signaling

Effector T cells are activated when their antigen-specific receptors and either the CD4 or CD8 co-receptors bind to peptide:MHC complexes. However, stimulation of naive T cells to proliferate and differentiate into armed effector T cells requires a co-stimulatory signal. Binding of a B7 molecule on the surface of an APC to a CD28 molecule on the surface of T cells is an example of molecular interaction which provides the required co-stimulatory signal.

Wild-type mice were pre-treated with blocking antibodies to the co-stimulatory molecules B7-1 and -2, then vaccinated as described in Example 1. $CD28^{-/-}$ mice were vaccinated as described in Example 1. As shown in FIG. 7, vaccination of wild-type mice pre-treated with blocking antibodies to B7-1 and B7-2, or vaccination of $CD28^{-/-}$ mice, resulted in a 52–80% reduction in CTL activity, compared to wild-type mice. These data indicate that the co-stimulatory signal provided by the B7-1/-2-CD28 interaction is required for ISS-mediated CTL activation.

Addition of anti-CD40 ligand (anti-CD40L) to the anti-B7-1/-2-treated mice, or to the $CD28^{-/-}$ mice had no effect on CTL activation, supporting the above conclusion that CD40/CD40-ligand interactions are not essential for ISS-mediated CTL activation.

IL-12 Contributes to ISS-mediated Priming of CTL

IL-12 is a pro-inflammatory cytokine produced by activated macrophages and other APC, and has been shown to promote priming of CTL.

$IL-12^{-/-}$ mice, wild-type mice, and $IL-12^{-/-}$ mice pre-treated with anti-B7-1/-2 antibody were vaccinated as described in Example 1. As shown in FIG. 8, $IL-12^{-/-}$ mice showed an 35% reduction in CTL activation, while $IL-12^{-/-}$ mice pre-treated with anti-B7-1/-2 antibody showed a 70% reduction in CTL activation, compared to wild-type mice. These data indicate that IL-12 contributes to ISS-mediated priming of CTL, but does not synergize with B7 signaling at the activation step.

The above results indicate that ISS-based vaccines bypass T cell help in this system by providing both co-stimulation and cross-presentation.

Example 6

Induction of Chemokines by Immunostimulatory Sequences (ISS)

Bone marrow derived macrophages (BMDM) were obtained from femurs of BALB/c mice and grown in tissue culture for one week. After one week in culture, BMDM were stimulated with ISS (1 µg/ml), M-ODN (control-ODN, 1 µ/ml), or lipopolysaccharide (LPS) (10 µg/ml). ISS has the sequence 5'-TGACTGTGAACGTTCGAGATGAB3' (SEQ ID NO:3); and mutated, control ODN )M-ODN) has the sequence 5'-TGACTGTGAACCTTCGAGATGAB3' (SEQ ID NO:6).

Twenty-four hours after stimulation, supernatants were collected and chemokine levels were detected and measured using an enzyme-linked immunosorbent assay (ELISA) from Pharmingen. The results are shown in Table 1, below.

TABLE 1

|  | MIP-1α (pg/ml) | MIP-1β (pg/ml) | RANTES (pg/ml) |
|---|---|---|---|
| Media | <100 | <200 | <2 |
| LPS | 310 ± 55 | 2810 ± 210 | 21 ± 5 |
| ISS-ODN (1 µg) | 4222 ± 350 | 4560 ± 1230 | 20 ± 8 |
| M-ODN (1 µg) | <100 | <200 | <2 |

The data presented in Table 1 show that BMDM from BALB/c mice exposed in culture to ISS secrete high levels of MIP-1α and MIP-1β, and lower levels of RANTES. The level of MIP-1α and MIP-1β secretion exceeded that from lipopolysaccharide (LPS)-treated BMDM. The level of RANTES secretion from ISS-LPS-treated BMDM was about the same. A mutant oligonucleotide lacking a critical CpG motif did not stimulate secretion of any of the chemokines tested.

Example 7

Induction of a gp120-specific Chemokine Response

Figure 9:
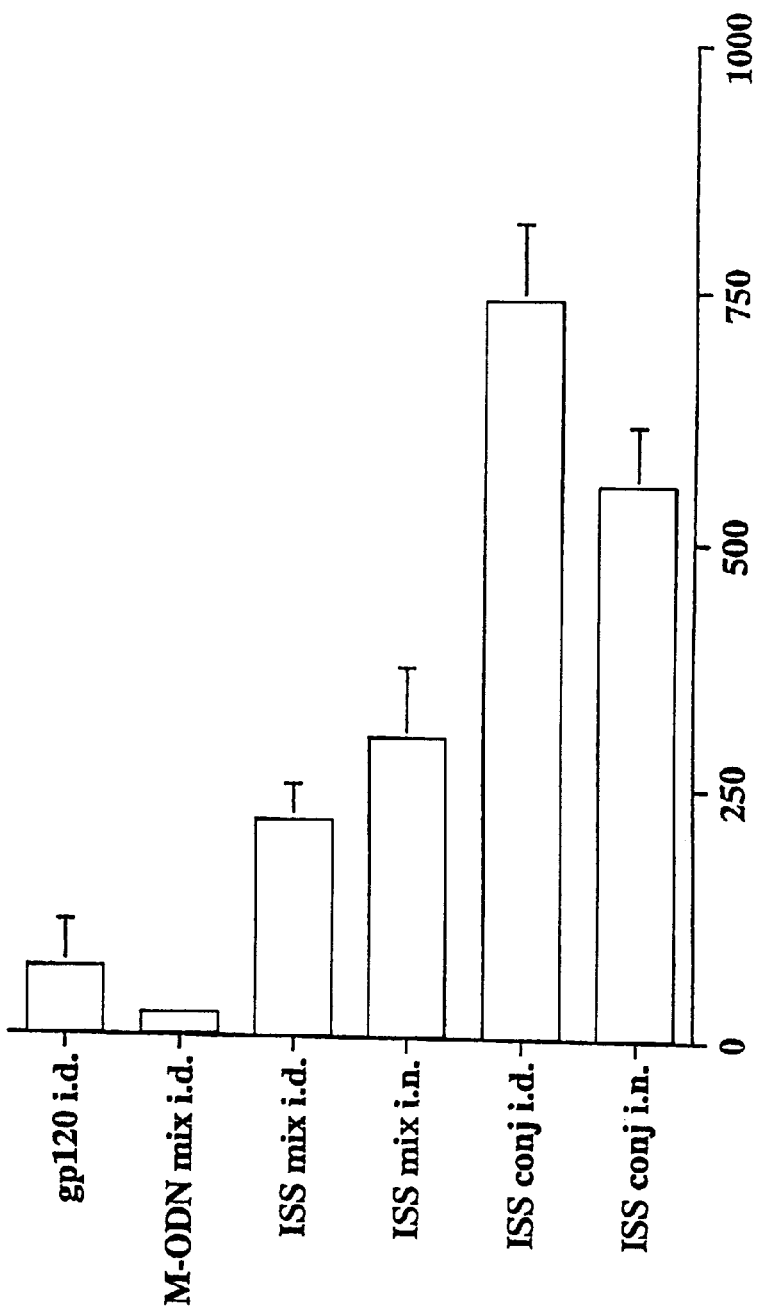
FIG. 9 is a bar graph depicting production of MIP1α by mouse splenocytes in response to immunization with ISS and gp120.
Figure 10:
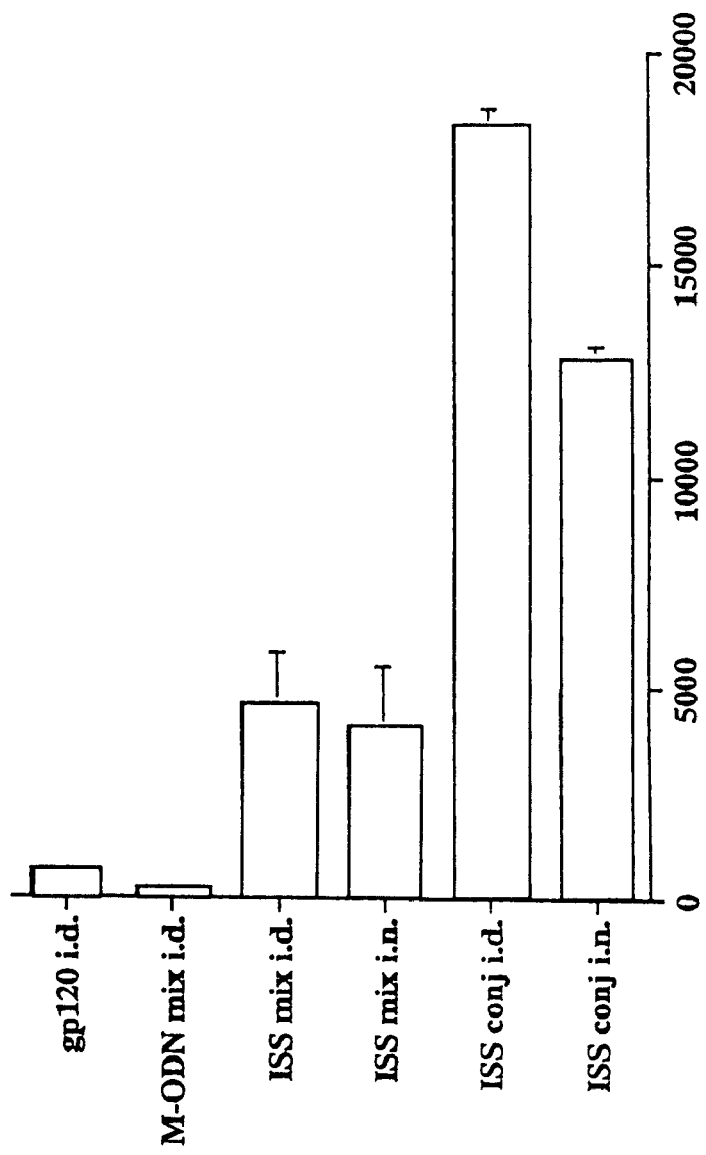
FIG. 10 is a bar graph depicting production of MIP1β by mouse splenocytes in response to immunization with ISS and gp120.
Figure 11:
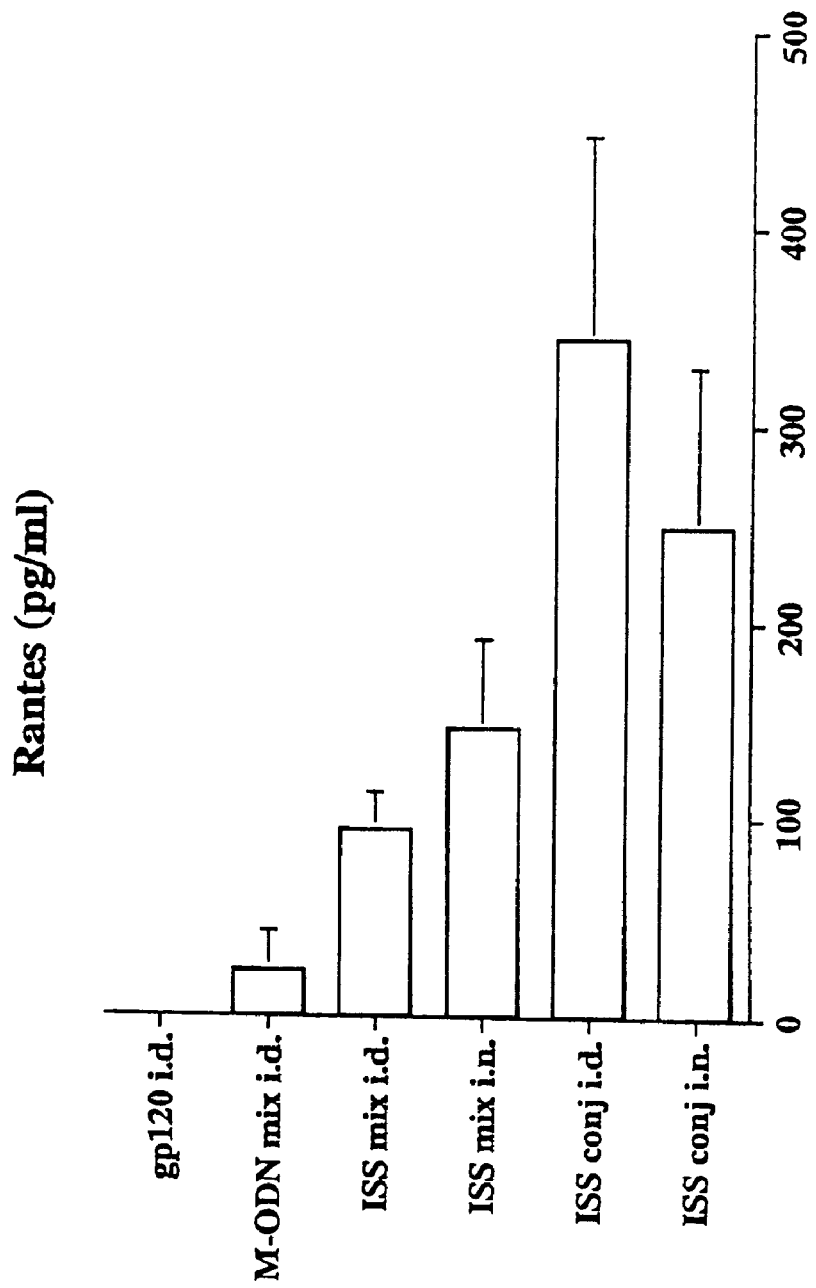
FIG. 11 is a bar graph depicting production of RANTES by mouse splenocytes in response to immunization with ISS and gp120.

Female BALB/c mice aged 4–6 weeks were immunized with gp120 (10 µg) alone, with gp120 with ISS (50 µg), or M-ODN (50 μg), or with gp120:ISS conjugate (10 μg based on gp120 content). Immunizations were given by either an intradermal (i.d.) or intranasal (i.n.) routes on 3 occasions spaced 2 weeks apart. Mice were sacrificed and splenocytes were isolated by routine methods at week 12. Gp120-specific chemokine responses by CD4+ cells were evaluated by incubation of 5×10$^5$ splenocytes in 96-well plates in a final volume of 200 μl of RPMI 1640 supplemented with gp120 at 10 μg/ml. In control cultures, splenocytes were incubated in RPMI 1640 without added gp120. Culture supernatants were harvested at 72 hours and analyzed by ELISA. The data are shown in FIGS. 9–11. MIP1α, MIP1β, and RANTES were detected at the indicated levels in supernatants of splenocytes isolated from mice administered with ISS mixed with gp120, or in supernatants of splenocytes from mice administered with ISS:gp120 conjugates, when the isolated splenocytes were cultured in the presence of gp120. Only very low levels of MIP1α, MIP1β, and RANTES could be detected in splenocytes isolated from mice administered with gp120 alone, or from mice administered with gp120 mixed with M-ODN. Neither MIP1α, MIP1β, nor RANTES was detected in supernatants of splenocytes cultured in the absence of gp120. The data demonstrate that splenocytes derived from mice immunized with ISS and gp120 (either as a mixture or as a conjugate) and cultured with gp120 produce CCR5-binding chemokines MIP1α, MIP1β, and RANTES in a gp120-specific manner. In contrast to the gp120-specific, CCR5 binding chemokine response (i.e., MIP1α, MIP1β, and RANTES) presented in FIGS. 9–11, the stem cell-derived factor-1 (SCF-1; a CXCR4-binding chemokine) was not produced by splenocytes cultured with gp120.

Example 8

Immunostimulatory DNA-based Vaccines Elicit Multi-faceted Immune Responses Against HIV at Systemic and Mucosal Sites Materials and Methods Reagents: HIV gp120 protein was obtained from Quality Biological, Inc. (Gaithersburg, Md.). ISS and mutated phosphorothioate oligodeoxynucleotides (mODN) were purchased from Trilink Biotechnologies (San Diego, Calif.). The sequence of the ISS used in these studies is 5'-TGACTGTGAACGTTCGAGATGA-3' (SEQ ID NO:3). The mODN has the sequence 5'-TGACTGTG AACCTTAGAGATGA-3' (SEQ ID NO:7). gp120:ISS and gp120:mODN conjugates were produced in a three-step process as previously described. Cho et al. (2000) *Nat. Biotech.* 18:509–514; and Gallucci et al. (1999) *Nat. Med.* 5:1249–1255. Introduction of maleimido groups onto gp120 molecules was achieved by incubation with a 20 molar excess of sulfo-SMCC (sulfosuccinimidyl 4-(N-maleimidomethyl)-cyclohexane-1-carboxylate) (Pierce Chemicals, Rockford, Ill.) for 2 hours followed by purification on a NAP-25 Column (Amersham-Pharmacia, Uppsala, Sweden). 5' activation of oligodeoxynucleotides was carried out by incubation with 0.2M TCEP (tricarboxyethylphosphine, Pierce Chemicals) and activated oligodeoxynucleotides were subsequently purified on a NAP-10 column. Maleimido-modified gp120 and thiol-activated oligodeoxynucleotides were then incubated together overnight, and free oligodeoxynucleotides were removed by filtration using an Amicon-50 spin column (Amicon, Inc., Beverly, Mass.). The conjugate was analyzed by SDS-PAGE. After electrophoresis, the samples were transferred onto nitrocellulose membranes and visualized by chemiluminescent detection of anti-gp120 antibody (Western blotting) or by autoradiography after hybridization with complementary $^{32}$P-γ-ATP-labeled oligodeoxynucleotides (Southwestern blotting).

Immunization protocols: Female BALB/c mice (Jackson Laboratories, Bar Harbor, Me.) aged 4–6 weeks were immunized with gp120 (10 μg) alone or with ISS (50 μg) or mODN (50 μg). Alternatively, mice were vaccinated with gp120:ISS or gp120:mODN conjugate (10 μg based on gp120 content). For intradermal (i.d.) immunization, reagents were delivered in 50 μl of saline by injection into the base of the tail. For intranasal (i.n.) vaccination, reagents were applied topically in 30 μl of saline divided equally and delivered to each nare of lightly anesthetized mice. Immunizations were delivered on 3 occasions spaced 2 weeks apart. For CD4 T cell depletion, mice received 1 mg of GK 1.5 mAb (Bio Express, West Lebanon, N.H.) intraperitoneally (i.p.) on 3 occasions, 4 weeks apart. With the use of flow cytometry, we determined that mice receiving GK 1.5 mAb, had <1% of the peripheral blood and splenic CD4 T cell counts of untreated mice throughout the course of these experiments. All animal procedures followed UCSD's animal care guidelines.

Sample collection and processing: Serum was obtained by retro-orbital bleeds during week 12. Vaginal washes were obtained during week 12 by lavage with 50 μL of PBS. Samples were spun to remove cellular debris, and frozen at −70° C. until the IgA assay was performed. Feces were collected at week 12 and IgA extracted by routine methods. Briefly, 3–6 pieces of freshly voided feces were collected and subsequently dried in a Speed Vac Concentrator. After drying, net dry weights were recorded, and the material was resuspended in PBS with 5% nonfat dry milk and protease inhibitors at a ratio of 20 μL/mg of feces to standardize for variability in the amount of fecal material collected. The solid matter was resuspended by vortexing for 12 hours followed by centrifugation at 16,000×g for 10 minutes to separate residual solids from supernatant. Supernatants were frozen at −70 C. until the IgA assay was performed.

Splenocytes (1×10$^8$/mouse), Peyer's patch lymphocytes (1×10$^7$/mouse), and lamina propria lymphocytes (1.5×10$^6$/moue) were recovered 12 weeks after the initiation of immunization, by routine methods. Briefly, spleens were harvested and teased to make single cell suspensions. Intestines were isolated, stripped of mesenteric fat, and Peyer's patches excised. The tissue was washed, and incubated in digestion media (collagenase VIII-300 U/ml, Sigma, St. Louis, Mo.; Dnase 1–1.5 μg/mL, Sigma) for 1 hour. Single cell suspensions were obtained by pouring the digestion mixture over a fine nylon sieve. Cells were subsequently washed and Peyer's patch lymphocytes separated on a 75%/40% Percoll gradient. Lamina propria lymphocytes were isolated by opening residual intestinal tissue longitudinally, washing extensively, cutting intestines into short segments, and incubating in 1 mM EDTA to remove the epithelial layer. After EDTA treatment, the tissue was washed in RPMI (Irvine Scientific, Irvine, Calif.) supplemented with 10% heat-inactivated fetal calf serum (Gibco BRL, Gaithersburg, Md.), 2 mM L-glutamine (Cellgro, Natham, Va.), 100 U/mL penicillin and 100 μg/mL streptomycin (Pen/Strep, Cellgro), and fungizone (Gibco BRL). The tissue was poured over a coarse sieve and residual tissue was incubated with digestion media. The lamina propria lymphocyte digestion mixture was poured over a fine nylon sieve to obtain a single cell suspension and then lymphocytes were purified on a 75%/40% Percoll gradient. These procedures resulted in >90% viability of all lymphocyte preparations.

Immunologic assays: Antibody levels were determined by routine ELISA techniques. Antibody levels are expressed in units/mL based on pooled high titer anti-gp120 standards. The undiluted IgG and IgG2a standards and the IgA standard were given arbitrary concentrations of 200,000, and 80,192 U/ml, respectively. Samples were compared to the standard curve on each plate using the DeltaSOFT II v. 3.66 program (Biometallics, Princeton, N.J.).

For CTL assays, $7 \times 10^6$ splenocytes, Peyer's patch lymphocytes, or lamina propria lymphocytes were cultured in supplemented RPMI with $6 \times 10^6$ mitomycin C-treated naive splenocytes in the presence of recombinant human IL-2 (50 IU/mL, PharMingen, San Diego, Calif.) and a HIV-1 class I ($H2^d$)-restricted gp120 peptide, (p18-I10; R-G-P-G-R-A-F-V-T-I; 4 µg/mL) (SEQ ID NO:8). After 5 days, restimulated cells were harvested and specific lysis of target cells was measured using the Cytotox 96 assay kit according to the manufacturer's instructions (Promega, Madison, Wis.).

IFNγ, MIP1α, and MIP1β responses were evaluated by incubation of splenocytes, Peyer's patch lymphocytes or lamina propria lymphocytes at $5 \times 10^5$ cells/ml in 96 well plates in a final volume of 200 µL of supplemented RPMI with gp120 (10 µg/mL) or p18–I10 (4 µg/mL). Culture supernatants were harvested at 72 hours and analyzed by ELISA for IFNγ (PharMingen), MIP1α, MIP1β, or RANTES content (R&D Systems, Inc., Minneapolis, Minn.), according to the manufacturers's recommendations. Each culture supernatant was compared to the standard curve on the plate using the DeltaSOFT II v. 3.66 program.

ELISPOT assays were performed using nitrocellulose-backed 96 well plates (Millipore, Bedford, Mass.). Plates were coated with 50 µl of PBS containing rat anti-mouse IFNγ antibody (PharMingen) at 10 µg/mL or goat anti-mouse MIP1α antibody (R&D) at 5 µg/mL and incubated overnight at 4° C. Wells were washed with BBS/0.05% Tween-20 and then blocked with 200 µL of supplemented RPMI for one hour at 37° C. Serial dilutions of splenocytes from each mouse starting at $2 \times 10^6$ cells/well were then plated and incubated in triplicate wells in media alone or with gp120 (10 µg/mL) or P18-I10 (4 µg/mL). After 24 hours, wells were washed and biotinylated anti-IFNγ (PharMingen) or biotinylated anti-MIP1α (R&D) was added to the appropriate wells for two hours at room temperature. Wells were then washed and horseradish peroxidase-streptavidin conjugate (Zymed, South San Francisco, Calif.) was added for one hour at room temperature. Plates were then developed by adding TMB Membrane Substrate (Kierkegaard and Perry Laboratories, Gaithersburg, Md.) per the manufacturer's instructions. Plates were dried and spots counted using a dissecting microscope. The number of peptide-specific cytokine-secreting cells was determined as a frequency of total CD8 T cells by using a correction factor based on the fraction of CD8 T cells present in spleens of untreated and CD4-depleted mice as determined by flow cytometry.

Statistical analyses: Statistical analyses were performed using the GraphPad Prism program (GraphPad Software, Inc., San Diego, Calif.). The significance of differences in means between multiple groups was determined using one-way analysis of variance (ANOVA) with Bonferroni's post-test analysis. When only two groups were compared, the significance of differences in means between the two groups was determined by unpaired t-test. Significant differences were defined as $p<0.05$.

Results

Synthesis of the gp120:ISS Conjugate

Because the optimal antigenic targets for HIV vaccine development have not yet been established, the present studies with gp120 represent a proof of principle for the application of ISS-based immunization strategies to the generation of improved immunity to other and better HIV target antigens as they are identified. We generated the gp120:ISS conjugate to determine whether ISS conjugation might generate an improved immune response to this relatively poorly immunogenic HIV antigen. ODNs containing ISS (7.5 kD) were conjugated to gp120 protein (120 kD) as described in the methods. Coomasie blue staining after SDS-PAGE of the gp120:ISS conjugate revealed a 140 kD band, reflecting a protein:ODN ratio of approximately 1:3. Western blot analysis with anti-gp120 antibody and southwestern blot analysis with radioactively labeled ODNs complementary to the ISS confirmed successful conjugation. Conjugation of gp120 to a non-stimulatory, mutated ODN (mODN) for use as a control was also performed and verified by the same methods.

Intradermal immunization with ISS-based gp120 vaccines elicits a Th1-biased immune response and chemokine secretion.

To determine if ISS could improve humoral and cytokine responses to gp120, BALB/c mice were immunized intradermally (i.d.) with co-administered gp120+ISS or with gp120:ISS conjugate. For comparison, control mice were immunized with gp120 alone, gp120+mODN, or gp120:mODN conjugate. In pilot experiments, ISS co-administered with gp120 at a dose similar to that present in the conjugate (1.3 µg of ISS per mouse), led to immune responses similar to those seen after immunization with gp120 alone. Therefore, in subsequent studies where unconjugated ISS was co-delivered with gp120, a 40-fold higher dose of ISS (50 µg) was used.

gp120 is a poor antigenic target for the generation of HIV neutralizing antibodies. Therefore, humoral immune responses to the vaccination reagents under study were determined by measuring antigen-specific total IgG and IgG2a (Th1 dependent) levels from serum collected twelve weeks after initiation of immunization (FIG. 12A). Compared with controls, mice i.d. immunized with gp120+ISS or gp120:ISS conjugate showed significantly higher levels of total IgG and IgG2a ($p<0.001$). In addition, both gp120+ISS co-administration and gp120:ISS immunization improved IgGI responses relative to control immunizations.

IFNγ production is a hallmark feature of Th1 biased immunity and contributes to protection against many viral infections. Therefore, the CD4 T cell IFNγ response of immunized mice was determined by culture of splenocytes with gp120 and analysis of supernatants by ELISA (FIG. 12B). IFNγ production was significantly higher for mice immunized with gp120+ISS ($p<0.05$) or gp120:ISS conjugate ($p<0.001$) vs. control immunized mice. Furthermore, gp120:ISS conjugate was more effective at inducing an IFNγ response than gp120+ISS ($p<0.001$).

The CCR5 chemokine receptor acts as a co-receptor for HIV entry into cells and competitive inhibition of this virus/co-receptor interaction by β-chemokines (MIP1α, MIP1β, and RANTES) inhibits the intercellular spread of HIV and the natural progression of the infection to AIDS. The ability of ISS to induce CCR5 specific β-chemokine production from macrophages in an antigen-independent manner led us to investigate whether ISS-based vaccines could elicit their antigen-specific production. Antigen-specific secretion of MIP1α, MIP1β, and RANTES was assessed by ELISA of supernatants from splenocytes cultured with gp120 (FIG. 12C and 12D). Mice immunized with gp120:ISS conjugate demonstrated significantly stronger MIP1α and MIP1β responses than controls (p<0.001) or gp120+ISS-immunized mice (p<0.001 for MIP1α and p<0.05 for MIP1β). However, while less effective then gp 120:ISS conjugate, gp120+ISS co-administration also elicited significant MIP1β but not MIP1α production. gp120-specific RANTES production was not appreciably induced above background levels in this series of experiments.

Intranasal immunization with ISS-based gp120 vaccines elicits systemic and mucosal immune responses.

Figure 13:
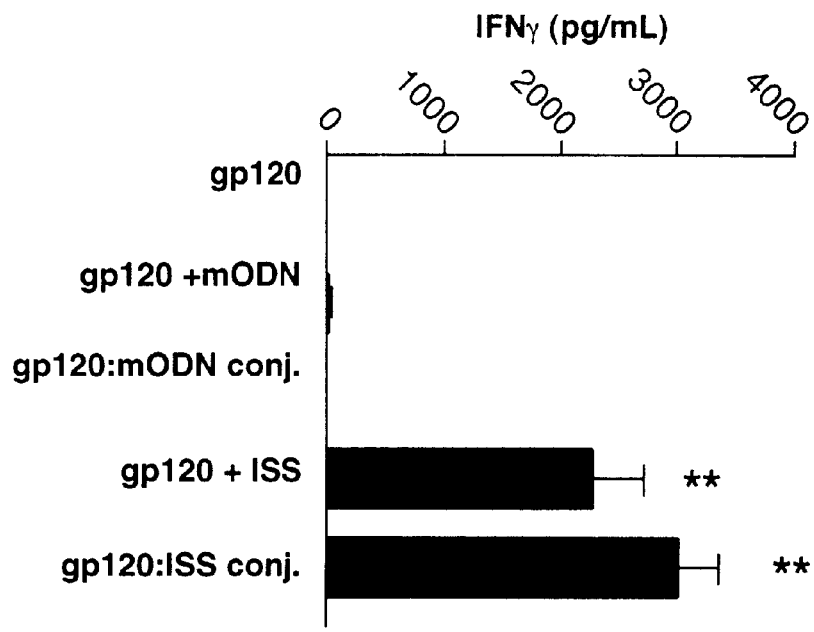
FIGS. 13A–E are graphs depicting systemic antigen-specific immunoglobulin (FIG. 13A), mucosal antigen-specific immunoglobulin (FIG. 13B), cytokine (FIG. 13C), and chemokine (FIGS. 13D and 13E) responses in mice immunized intranasally with ISS-based gp120 vaccines.
Figure 13:
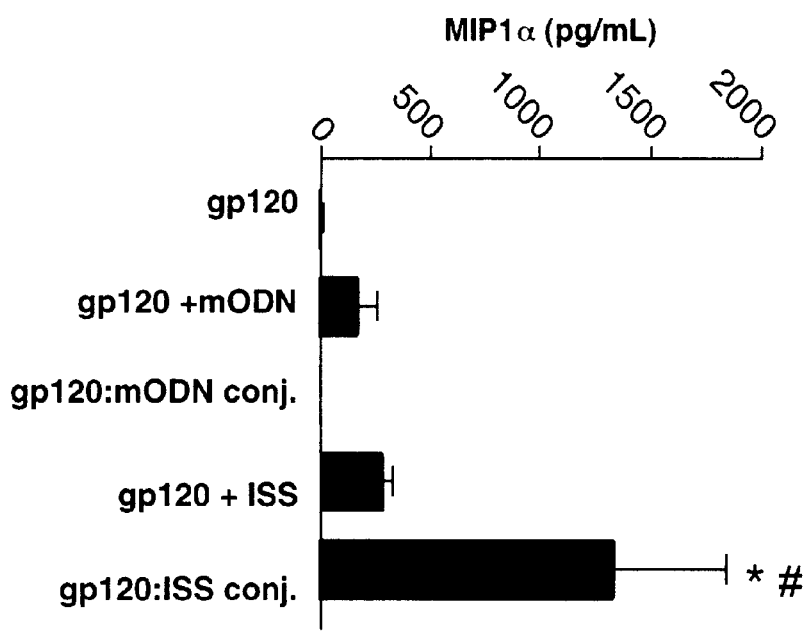

Protection against HIV infection is likely to require immunity at mucosal sites, as 1) its spread is principally by sexual transmission, 2) the intestinal mucosa represents an important site for the initial replication of the virus, and 3) mucosal but not systemic immunity provides protection against mucosal challenge in models of viral infection. As mucosal immunity is best elicited by vaccine delivery to mucosal sites, the immunization reagents described in the previous sections were administered intranasally (i.n.) to mice at the same doses used for i.d. immunization, and both systemic and mucosal immune parameters were measured. Similar to i.d. immunization, i.n. immunization with gp120+ ISS or gp120:ISS conjugate elicited significantly higher levels of serum IgG and IgG2a than controls (p<0.001) (FIG. 13A). However, unlike i.d. immunization, i.n. immunization with gp120+ISS induced a weaker IgG (p<0.05) and IgG2a (p<0.001) response than the conjugate. Furthermore, i.n. vaccination with gp120/ISS or gp120:ISS conjugate also induced a vigorous secretory IgA response detected in vaginal washes and fecal samples (p<0.001 vs. controls) (FIG. 13B). In contrast, i.d. vaccination with these reagents failed to elicit a significant mucosal IgA response. Finally, i.n. immunization with either gp120+ISS or gp120:ISS conjugate elicited significantly more gp120-specific IFNγ, MIP1α, and MIP1β production than control vaccinations (p<0.001 for IFNγ, p<0.05 for MIP1α and MIP1β; FIGS. 13C–E).

ISS-based gp120 vaccines elicit systemic and mucosal CTL activity.

Figure 14:
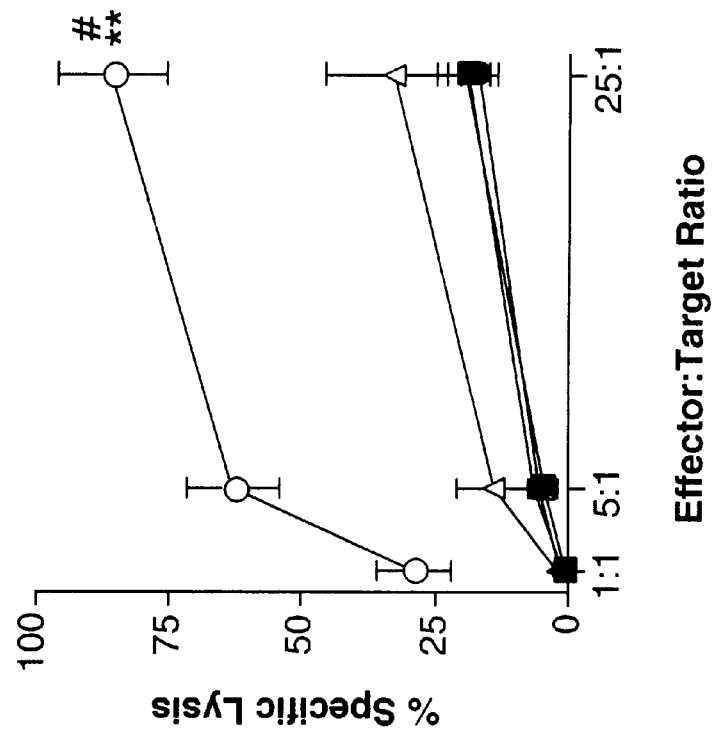
FIGS. 14A–D are graphs depicting splenic and mucosal CTL activity in mice immunized intradermally (FIG. 14A) or intranasally (FIG. 14B). Mucosal CTL activity from lamina propria (FIG. 14C) and Peyer's patch (FIG. 14D) lymphocytes was determined 12 weeks after initiation of i.n. or i.d. immunization.
Figure 14:
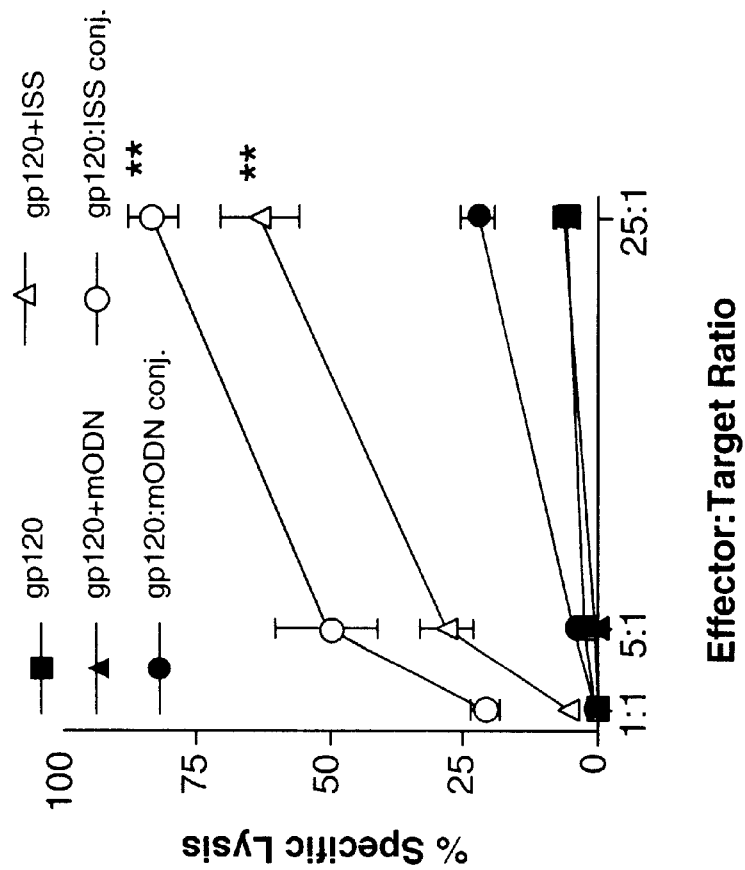
Figure 14:
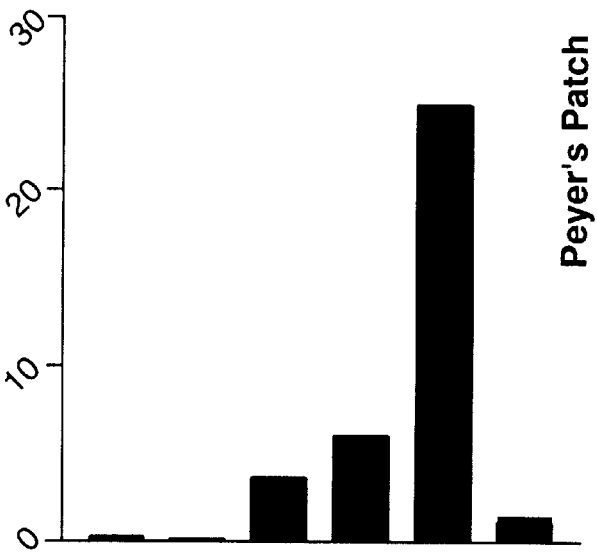
Figure 14:
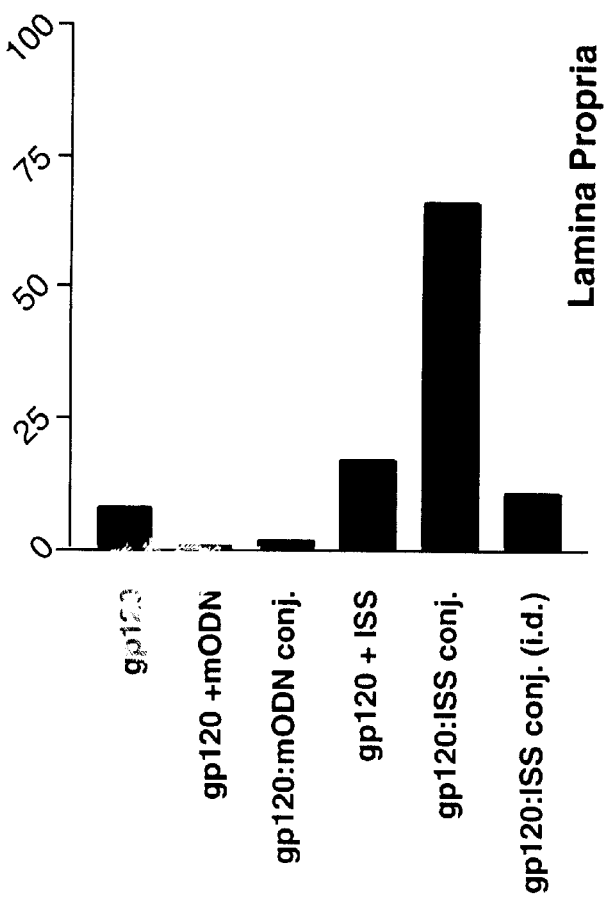

Since an effective CD8 CTL response is important in preventing and controlling HIV infection, the ability of ISS-based gp120 immunization to elicit antigen-specific CTL activity was next determined. Both i.d. (FIG. 14A) and i.n. (FIG. 14B) administration of gp120:ISS conjugate elicited similar levels of high specific lysis in splenic CTL assays. However, while i.d. administration of gp120+ISS elicited CTL activity that was similar to the conjugate, i.n. administration of gp120+ISS elicited a significantly lower CTL response (p<0.05). In addition to systemic CTL activity, i.n. gp120:ISS conjugate delivery and to a much lesser extent gp120+ISS co-administration induced mucosal CTL responses as measured with lamina propria (FIG. 14C) and Peyer's patch lymphocytes (FIG. 14D). However, consistent with the poor secretory IgA response seen after systemic vaccination, both i.d. gp120+ISS and gp120:ISS conjugate immunizations induced only weak CTL responses at these mucosal sites.

ISS-based gp120 vaccines elicit MHC class I-restricted cytokine and chemokine responses.

The cytokine and chemokine data described in the previous sections reflect MHC class II-dependent responses, as intact gp120 protein was used to stimulate cells. Cytokine and chemokine secretion by CD 8 T cells, in addition to CTL responses, are important for controlling HIV infection, while CD4 T cell deficiency is a characteristic feature of AIDS.

Figure 15:
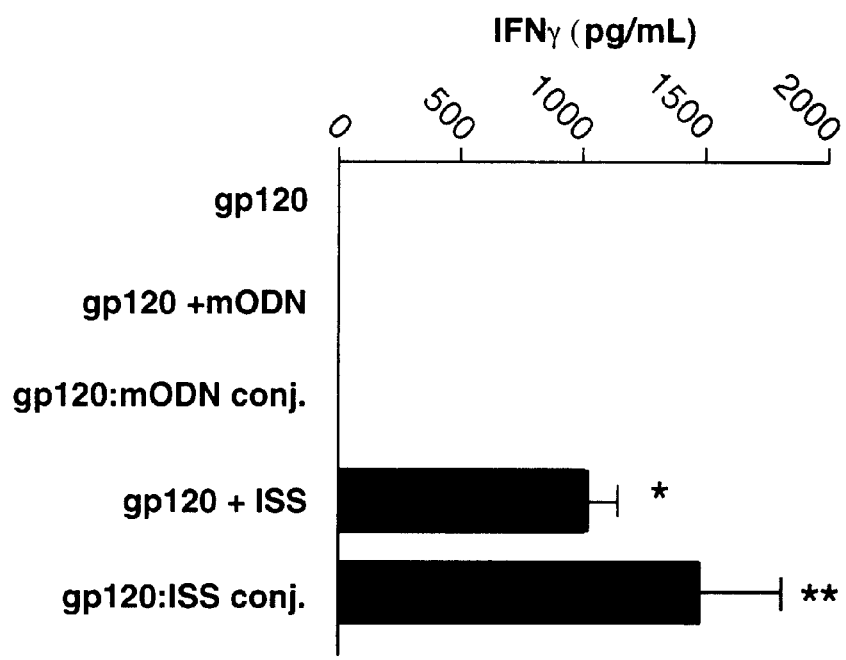
FIGS. 15A–C are graphs depicting MHC Class I-restricted IFNγ (FIG. 1 5A) and chemokine (FIGS. 15B and 15C) responses in mice immunized intradermally with ISS-based gp120 vaccines.
Figure 15:
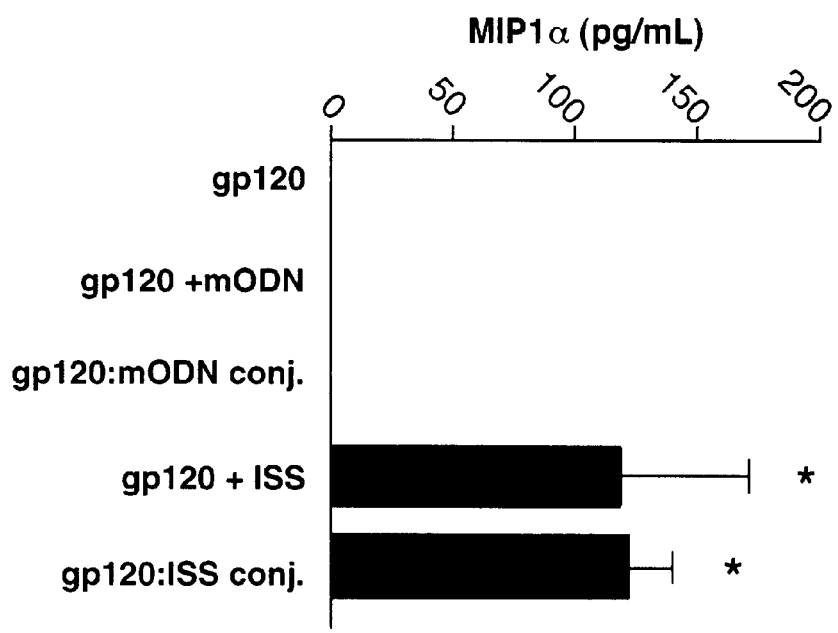

Therefore, the ability of ISS-based vaccines to induce cytokine and chemokine responses from CD8 T cells was investigated. Splenocytes from immunized mice were restimulated in vitro with MHC class I ($H2^d$)-restricted gp120 peptide and cytokine and chemokine production in culture supernatants was subsequently determined by ELISA (FIGS. 15A–C). Mice immunized i.d. with either gp120+ISS or gp120:ISS conjugate demonstrated significant CD8 T cell production of IFNγ, MIP1α, and MIP1β compared to control immunized mice. Similar results were seen with i.n. gp120+ISS and gp120:conjugate vaccination.

The class I restricted cytokine, chemokine, and CTL responses elicited by gp120:ISS immunization are CD4 T cell-independent.

Figure 16A:
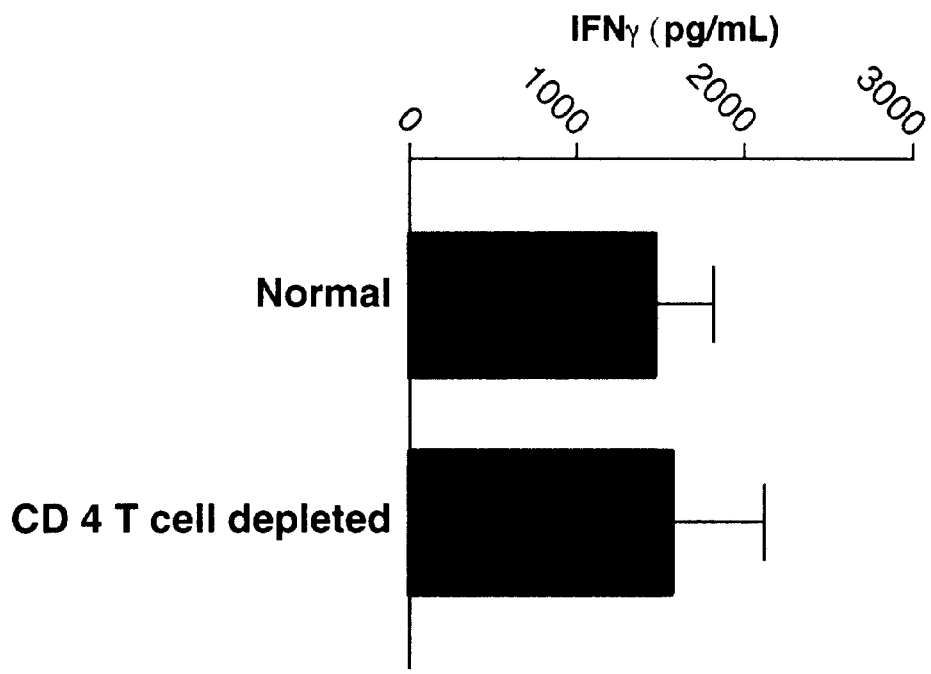
FIGS. 16A–E are graphs depicting MHC Class I-restricted cytokine (FIGS. 16A and 16D), chemokine (FIGS. 16B, C, and D) and CTL activity (FIG. 16E) elicited by gp120:ISS vaccination in normal (untreated) or CD4-depleted (treated with anti-CD4 Ab) mice.
Figure 16B:
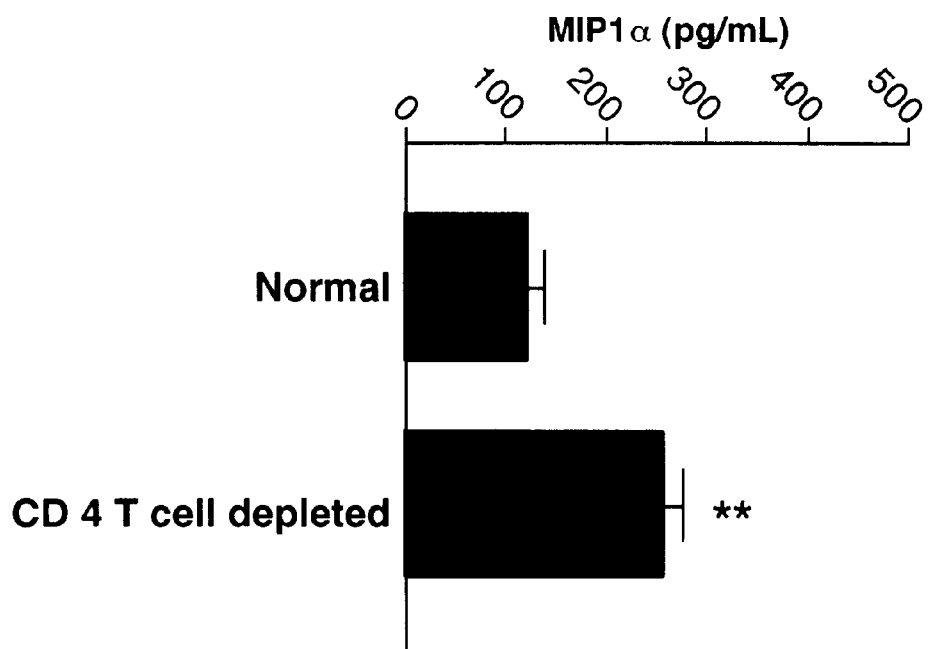
Figure 16:
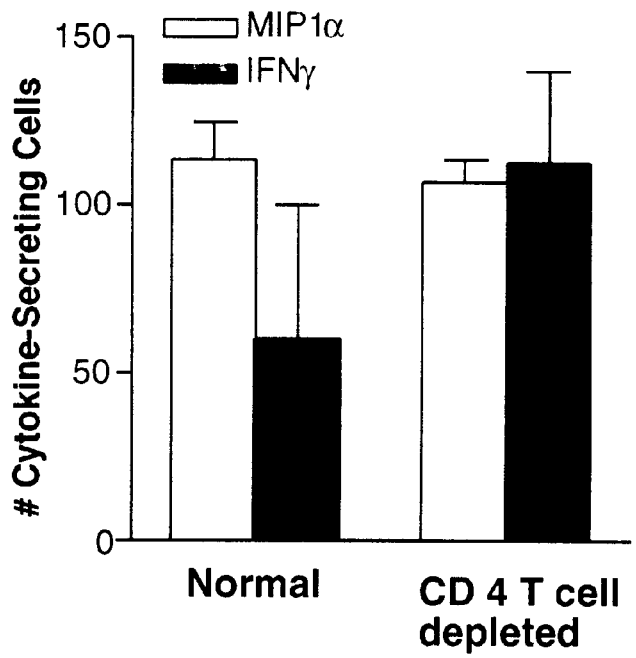
Figure 16:
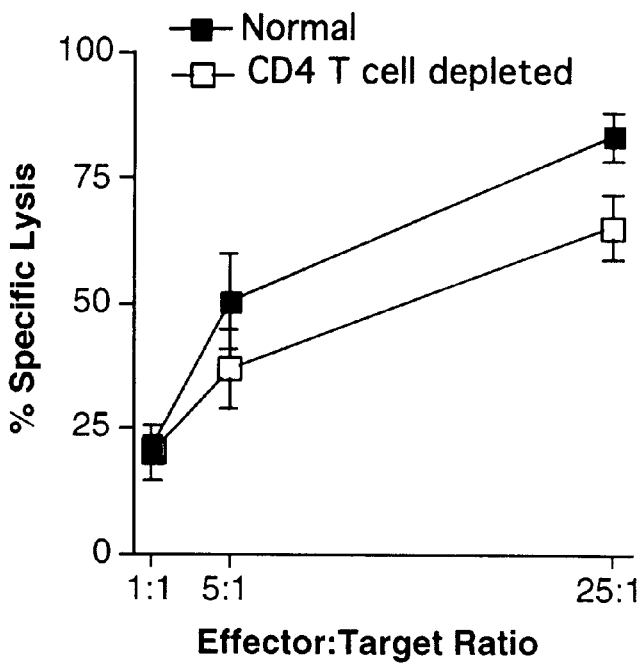

During the course of HIV infection, CD4 T cells are depleted. Therefore, it would be important for a therapeutic AIDS vaccine to elicit robust immunity in the absence of CD4 T cells. The ability of ISS-based vaccines to elicit cytokine, chemokine, and CTL responses from CD8 T cells led us to investigate whether these responses required CD4 T cell help. Previous investigations have demonstrated that ovalbumin:ISS (OVA:ISS) conjugate vaccination induces equivalent CTL responses in CD4 knockout and wild type mice, while the CTL response of OVA+ISS vaccinated CD4 knockout mice is compromised. Therefore, gp120:ISS conjugate was used to i.d. immunize mice depleted of CD4 T cells with anti-CD4 mAb and non-CD4 T cell depleted mice, to compare their CD8 T cell responses. Splenocytes from gp120:ISS conjugate immunized CD4 T cell-depleted mice that were restimulated with a class I restricted gp120 peptide demonstrated a retained ability to secrete antigen-specific IFNγ (FIG. 16A), MIP1α (FIG. 16B), and MIP1β (FIG. 16C) relative to splenocytes from immunized mice that were not CD4 T cell depleted.

Furthermore, by ELISPOT analysis, gp120:ISS conjugate immunized CD4 T cell depleted and non-CD4 T cell depleted mice had equivalent frequencies of CD8 T cells producing IFNγ and MIP1α in response to incubation with a class I restricted gp120 peptide (FIG. 16D). Consistent with these results, antigen-specific CTL activity was also retained in CD4 T cell depleted mice (FIG. 16E). As expected, restimulation of splenocytes from immunized CD4 T cell depleted mice with gp120 protein failed to elicit cytokine or chemokine responses. Furthermore, CD4 T cell depleted mice were unable to generate a detectable antibody response after gp120:ISS conjugate immunization in spite of their development of CD8 T cell immunity. Similar to i.d. immunized mice, CD4 T cell depleted mice immunized i.n. with gp120:ISS conjugate also showed retained CD8 T cell responses.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A method of increasing antigen-specific T lymphocyte activity in a CD4+ T cell-deficient individual, comprising administering a formulation comprising an immunostimulatory nucleic acid molecule and an antigen in an amount effective to increase antigen-specific CTL activity, wherein the immunostimulatory nucleic acid is covalently linked to the antigen.

2. The method of claim 1, wherein the immunostimulatory nucleic acid comprises the sequence 5' C-G 3'.

3. The method of claim 1, wherein the antigen is associated with an intracellular pathogen.

4. The method of claim 1, wherein the antigen is a tumor-associated antigen.

5. The method of claim 1, wherein the immunostimulatory nucleic acid molecule comprises a nucleotide sequence selected from the group consisting of 5'-purine-purine-cytosine-guanine-pyrimidine-pyrimidine-3'; 5'-purine-TCG-pyrimidine-pyrimidine-3'; and 5'-$(TGC)_n$-3', where $n \geqq 1$.

6. The method of claim 1, wherein the individual has a reduced number of $CD4^+$ T lymphocytes due to a primary immunodeficiency.

7. The method of claim 1, wherein the individual has a reduced number of $CD4^+$ T lymphocytes due to an acquired immunodeficiency.

8. The method of claim 7, wherein the acquired immunodeficiency is a temporary immunodeficiency due to a treatment selected from the group consisting of radiation therapy to treat a cancer, chemotherapy to treat a cancer, immunosuppression following bone marrow transplantation, immunosuppression caused by treatment for an autoimmune disease, and immunosuppression following organ transplantation.

9. The method of claim 7, wherein the acquired immunodeficiency is acquired immunodeficiency syndrome.

10. The method of claim 1, wherein said immunostimulatory nucleic acid molecule is administered to a mucosal tissue.

11. The method of claim 1, wherein said immunostimulatory nucleic acid molecule is administered systemically.

* * * * *

UNITED STATES PATENT AND TRADEMARK OFFICE
CERTIFICATE OF CORRECTION

PATENT NO.    : 6,534,062 B2
DATED         : March 18, 2003
INVENTOR(S)   : Raz, Eyal et al.

It is certified that error appears in the above-identified patent and that said Letters Patent is hereby corrected as shown below:

<u>Column 45,</u>
Lines 30-36, Claim 1 should read:
1. A method of increasing antigen-specific cytotoxic T lymphocyte (CTL) activity in a $CD4^+$ T cell-deficient individual, comprising administering to the individual a formulation comprising an immunostimulatory nucleic acid molecule and an antigen in an amount effective to increase antigen-specific CTL activity, wherein the immunostimulatory nucleic acid molecule is covalently linked to the antigen.
Lines 43-47, Claim 5 should read:
5. The method of claim 1, wherein the immunostimulatory nucleic acid molecule comprises a nucleotide sequence selected from the group consisting of 5'-purine-purine-cytosine-guanine– pyrimidine-pyrimidine-3'; 5'-purine-TCG-pyrimidine-pyrimidine-3'; and 5'-(T<u>C</u>G)$_n$-3', where n$\geq$1.

Signed and Sealed this

Twelfth Day of August, 2003

JAMES E. ROGAN
*Director of the United States Patent and Trademark Office*